United States Patent
Kravtchenko et al.

(10) Patent No.: US 7,338,534 B2
(45) Date of Patent: Mar. 4, 2008

(54) OXIDATION DYEING COMPOSITION FOR KERATINOUS FIBRES BASED ON AMPHIPHILIC POLYMERS OF AT LEAST AN ETHYLENICALLY UNSATURATED MONOMER WITH SULPHONIC GROUP AND COMPRISING A HYDROPHOBIC PART

(75) Inventors: Sylvain Kravtchenko, Asnieres (FR); Alain Lagrange, Coupvray (FR)

(73) Assignee: L'Oreal, Paris (FR)

( * ) Notice: Subject to any disclaimer, the term of this patent is extended or adjusted under 35 U.S.C. 154(b) by 52 days.

(21) Appl. No.: 10/450,703

(22) PCT Filed: Dec. 19, 2001

(86) PCT No.: PCT/FR01/04075

§ 371 (c)(1),
(2), (4) Date: Jan. 12, 2004

(87) PCT Pub. No.: WO02/051367

PCT Pub. Date: Jul. 4, 2002

(65) Prior Publication Data

US 2005/0086745 A1    Apr. 28, 2005

(30) Foreign Application Priority Data

Dec. 22, 2000 (FR) .................................. 00 16949
Jan. 11, 2001 (FR) .................................. 01 00326

(51) Int. Cl.
*A61K 7/13* (2006.01)
(52) U.S. Cl. ...................... 8/405; 8/406; 8/410; 8/411; 8/415; 8/421; 8/552; 8/554; 8/555; 8/558; 8/592; 424/70.17; 132/202
(58) Field of Classification Search ................ 8/405, 8/406, 510, 411, 415, 421, 552, 554, 555, 8/557, 558, 592, 410; 424/70.17; 132/202
See application file for complete search history.

(56) References Cited

U.S. PATENT DOCUMENTS

| 4,460,732 A | 7/1984 | Buscall et al. ............... 524/460 |
|---|---|---|
| 4,861,499 A | 8/1989 | Neff et al. ............... 252/8.581 |
| 5,089,578 A | 2/1992 | Valint et al. ................. 526/240 |
| 5,114,706 A | 5/1992 | Duvel .......................... 424/70 |
| 5,464,452 A | 11/1995 | Cole et al. ....................... 8/495 |
| 5,609,862 A | 3/1997 | Chen et al. |
| 5,932,201 A | 8/1999 | de Labbey et al. ...... 424/70.17 |
| 5,976,195 A * | 11/1999 | de la Mettrie et al. ......... 8/411 |
| 6,149,900 A | 11/2000 | Afriat et al. |
| 6,180,118 B1 | 1/2001 | Maubru |
| 2001/0023514 A1* | 9/2001 | Cottard et al. ................. 8/406 |

FOREIGN PATENT DOCUMENTS

| EP | 0 406 042 | 1/1991 |
|---|---|---|
| EP | 0 750 899 | 1/1997 |
| EP | 0750 899 A2 * | 1/1997 |
| EP | 0 815 843 | 1/1998 |
| EP | 0 823 250 | 2/1998 |
| EP | 0 970 685 | 1/2000 |
| EP | 1 055 406 | 11/2000 |
| FR | 2 753 372 | 3/1998 |
| JP | 5-246828 | 9/1993 |
| JP | 6-107526 | 4/1994 |
| JP | 8-252447 | 10/1996 |
| JP | 10-101532 | 4/1998 |
| JP | 11-180824 | 7/1999 |
| WO | 00/31154 | 6/2000 |
| WO | WO 00/37041 | 6/2000 |

OTHER PUBLICATIONS

Kobayashi, Atsushi et al. "Solubilization Properties of N-substituted Amphiphilic Acrylamide Copolymers", J. Appl. Polym. Sci., vol. 73, No. 12, pp. 2447-2453 1999.
U.S. Appl. No. 10/450,703, filed Jun. 23, 2003, Kravtchenko et al.
U.S. Appl. No. 10/451,409, filed Jun. 23, 2003, Kravtchenko et al.

* cited by examiner

*Primary Examiner*—Eisa Elhilo
(74) *Attorney, Agent, or Firm*—Oblon, Spivak, McClelland, Maier & Neustadt, P.C.

(57) ABSTRACT

The invention concerns an oxidation dyeing composition for keratinous fibres, in particular for human keratinous fibres and more particularly hair, comprising, in a medium suited for dyeing, at least an oxidation dyeing agent, and also at least an amphiphilic polymer including at least an ethylenically unsaturated monomer with a sulphonic group, in free form or partly or completely neutralised and further at least a hydrophobic part. The invention also concerns dyeing methods and devices using said composition.

89 Claims, No Drawings

OXIDATION DYEING COMPOSITION FOR KERATINOUS FIBRES BASED ON AMPHIPHILIC POLYMERS OF AT LEAST AN ETHYLENICALLY UNSATURATED MONOMER WITH SULPHONIC GROUP AND COMPRISING A HYDROPHOBIC PART

The present invention relates to a composition for the oxidation dyeing of keratin fibers, in particular human keratin fibers and more particularly the hair, comprising at least one oxidation dye and at least one amphiphilic polymer comprising at least one ethylenically unsaturated monomer containing a sulfonic group, in free form or partially or totally neutralized form, and also at least one hydrophobic portion.

It is known practice to dye keratin fibers, and in particular human hair, with dye compositions containing oxidation dye precursors, generally known as "oxidation bases", in particular ortho- or para-phenylenediamines, ortho- or para-aminophenols, and heterocyclic bases.

Oxidation dye precursors are compounds that are initially uncolored or only weakly colored, which develop their dyeing power on the hair in the presence of oxidizing agents, leading to the formation of colored compounds. The formation of these colored compounds results either from an oxidative condensation of the "oxidation bases" with themselves or from an oxidative condensation of the "oxidation bases" with coloration modifiers, or "couplers", which are generally present in the dye compositions used in oxidation dyeing and are represented more particularly by meta-phenylenediamines, meta-aminophenols and meta-diphenols, and certain heterocyclic compounds.

The variety of molecules used, which consist on the one hand of the "oxidation bases" and on the other hand of the "couplers", allows a very wide range of colors to be obtained.

To localize the oxidation dye product on application to the hair so that it does not run down the face or beyond the areas that it is proposed to dye, use has been made hitherto of conventional thickeners such as crosslinked polyacrylic acid, hydroxyethylcelluloses, certain polyurethanes, waxes or mixtures of nonionic surfactants with an HLB (Hydrophilic-Lipophilic Balance) value, which, when suitably chosen, give rise to a gelling effect when they are diluted with water and/or surfactants.

However, the Applicant has found that the thickening systems mentioned above do not make it possible to obtain intense and chromatic shades of low selectivity and good staying power, while at the same time leaving the treated hair in a good cosmetic condition. Moreover, the Applicant has also found that ready-to-use dye compositions containing the oxidation dye(s) and the thickening systems of the prior art do not allow a sufficiently precise application without running or reductions in viscosity over time.

After considerable research conducted in this matter, the Applicant has now discovered that it is possible to obtain ready-to-use oxidation dye compositions that do not run and thus remain satisfactorily localized at the point of application, and that also make it possible to obtain powerful and chromatic (luminous) shades with low selectivity and good staying power with respect to chemical agents (shampoos, permanent-waving agents, etc.) or natural agents (light, perspiration, etc.) while at the same time giving the hair good cosmetic properties, if an effective amount of an amphiphilic polymer comprising at least one ethylenically unsaturated monomer containing a sulfonic group, in free form or partially or totally neutralized form, and also at least one hydrophobic portion, is introduced either (i) into the composition containing the oxidation dye(s) and optionally the coupler(s) [or composition A], or (ii) into the oxidizing composition [or composition B], or (iii) into both compositions at the same time.

The Applicant has also found that the mixing of the dye compositions with the oxidizing agents is facilitated by the presence of the amphiphilic polymers according to the invention.

These discoveries form the basis of the present invention.

One subject of the present invention is thus an oxidation dye composition for keratin fibers, in particular for human keratin fibers and particularly the hair, comprising at least one oxidation dye in a medium that is suitable for dyeing, which is characterized in that it also comprises at least one amphiphilic polymer comprising at least one ethylenically unsaturated monomer containing a sulfonic group, in free form or partially or totally neutralized form, and also at least one hydrophobic portion.

Another subject of the invention relates to a ready-to-use composition for dyeing keratin fibers, which comprises at least one oxidation dye, at least one oxidizing agent and at least one amphiphilic polymer comprising at least one ethylenically unsaturated monomer containing a sulfonic group, in free form or partially or totally neutralized form, and also at least one hydrophobic portion.

For the purposes of the invention, the expression "ready-to-use composition" means the composition intended to be applied in unmodified form to the keratin fibers, i.e. it may be stored in unmodified form before use, or may result from the extemporaneous mixing of two or more compositions.

The invention is also directed toward a process for dyeing keratin fibers, in particular human keratin fibers such as the hair, which consists in applying to the fibers at least one dye composition comprising at least one oxidation dye in a medium that is suitable for dyeing, the color being developed at alkaline, neutral or acidic pH using an oxidizing composition comprising at least one oxidizing agent, which is mixed with the dye composition just at the time of use or which is applied sequentially without intermediate rinsing, at least one amphiphilic polymer comprising at least one ethylenically unsaturated monomer containing a sulfonic group, in free form or partially or totally neutralized form, and also at least one hydrophobic portion, being present in the dye composition or in the oxidizing composition or in each of the two compositions.

A subject of the invention is also dyeing devices or multicompartment "kits".

A two-compartment device according to the invention comprises one compartment containing a dye composition comprising at least one oxidation dye in a medium that is suitable for dyeing, and another compartment containing an oxidizing composition comprising an oxidizing agent in a medium that is suitable for dyeing, the amphiphilic polymer according to the invention being present in the dye composition or in the oxidizing composition or in each of the two compositions.

Another device, containing three compartments, according to the invention comprises a first compartment containing a dye composition comprising at least one oxidation dye in a medium that is suitable for dyeing, a second compartment containing an oxidizing composition comprising at least one oxidizing agent in a medium that is suitable for dyeing, and a third compartment containing a composition comprising at least one amphiphilic polymer according to the invention described above, in a medium that is suitable for dyeing, the dye composition and/or the oxidizing composition also possibly comprising an amphiphilic polymer according to the invention.

However, other characteristics, aspects, subjects and advantages of the invention will emerge even more clearly on reading the description and the examples that follow.

Amphiphilic Polymers According to the Invention

The polymers in accordance with the invention are amphiphilic polymers comprising at least one ethylenically unsaturated monomer containing a sulfonic group, in free form or partially or totally neutralized form and comprising at least one hydrophobic portion.

The expression "amphiphilic polymer" means any polymer comprising both a hydrophilic portion and a hydrophobic portion and especially a fatty chain.

The hydrophobic portion present in the polymers of the invention preferably contains from 6 to 50 carbon atoms, more preferably from 6 to 22 carbon atoms, even more preferably from 6 to 18 carbon atoms and more particularly from 12 to 18 carbon atoms.

Preferably, the polymers in accordance with the invention are partially or totally neutralized with a mineral base (sodium hydroxide, potassium hydroxide or aqueous ammonia) or an organic base such as mono-, di- or triethanolamine, an aminomethylpropanediol, N-methylglucamine, basic amino acids, for instance arginine and lysine, and mixtures of these compounds.

The amphiphilic polymers in accordance with the invention generally have a number-average molecular weight ranging from 1000 to 20 000 000 g/mol, preferably ranging from 20 000 to 5 000 000 and even more preferably from 100 000 to 1 500 000 g/mol.

The amphiphilic polymers according to the invention may or may not be crosslinked. Crosslinked amphiphilic polymers are preferably chosen.

When they are crosslinked, the crosslinking agents may be chosen from polyolefinically unsaturated compounds commonly used for the crosslinking of polymers obtained by free-radical polymerization.

Mention may be made, for example, of divinylbenzene, diallyl ether, dipropylene glycol diallyl ether, polyglycol diallyl ethers, triethylene glycol divinyl ether, hydroquinone diallyl ether, ethylene glycol di(meth)acrylate or tetraethylene glycol di(meth)acrylate, trimethylolpropane triacrylate, methylenebisacrylamide, methylenebismethacrylamide, triallylamine, triallyl cyanurate, diallyl maleate, tetraallylethylenediamine, tetraallyloxyethane, trimethylolpropane diallyl ether, allyl (meth)acrylate, allylic ethers of alcohols of the sugar series, or other allyl or vinyl ethers of polyfunctional alcohols, and also allylic esters of phosphoric and/or vinylphosphonic acid derivatives, or mixtures of these compounds.

Methylenebisacrylamide, allyl methacrylate or trimethylolpropane triacrylate (TMPTA) will be used more particularly. The degree of crosslinking will generally range from 0.01 mol % to 10 mol % and more particularly from 0.2 mol % to 2 mol % relative to the polymer.

The ethylenically unsaturated monomers containing a sulfonic group are chosen especially from vinylsulfonic acid, styrenesulfonic acid, (meth)acrylamido($C_1$-$C_{22}$)alkylsulfonic acids, and N—($C_1$-$C_{22}$)alkyl(meth)acrylamido($C_1$-$C_{22}$)alkylsulfonic acids, for instance undecylacrylamidomethanesulfonic acid, and also partially or totally neutralized forms thereof.

(Meth)acrylamido($C_1$-$C_{22}$)alkylsulfonic acids such as, for example, acrylamidomethanesulfonic acid, acrylamidoethanesulfonic acid, acrylamidopropane-sulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid or 2-acrylamido-2,6-dimethyl-3-heptanesulfonic acid, and also partially or totally neutralized forms thereof, will more preferably be used.

2-Acrylamido-2-methylpropanesulfonic acid (AMPS), and also partially or totally neutralized forms thereof, will more particularly be used.

The amphiphilic polymers in accordance with the invention may be chosen especially from random amphiphilic AMPS polymers modified by reaction with a $C_6$-$C_{22}$ n-monoalkylamine or di-n-alkylamine, and such as those described in patent application WO-A-00/31154 (forming an integral part of the content of the description). These polymers may also contain other ethylenically unsaturated hydrophilic monomers chosen, for example, from (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

The preferred polymers of the invention are chosen from amphiphilic copolymers of AMPS and of at least one ethylenically unsaturated hydrophobic monomer comprising at least one hydrophobic portion containing from 6 to 50 carbon atoms, more preferably from 6 to 22 carbon atoms, even more preferably from 6 to 18 carbon atoms and more particularly 12 to 18 carbon atoms.

These same copolymers may also contain one or more ethylenically unsaturated monomers not comprising a fatty chain, such as (meth)acrylic acids, β-substituted alkyl derivatives thereof or esters thereof obtained with monoalcohols or mono- or polyalkylene glycols, (meth)acrylamides, vinylpyrrolidone, maleic anhydride, itaconic acid or maleic acid, or mixtures of these compounds.

These copolymers are described especially in patent application EP-A-750 899, patent U.S. Pat. No. 5,089,578 and in the following publications from Yotaro Morishima:

"Self-assembling amphiphilic polyelectrolytes and their nanostructures—Chinese Journal of Polymer Science Vol. 18, No. 40, (2000), 323-336";

"Micelle formation of random copolymers of sodium 2-(acrylamido)-2-methylpropanesulfonate and a nonionic surfactant macromonomer in water as studied by fluorescence and dynamic light scattering—Macromolecules 2000, Vol. 33, No. 10-3694-3704";

"Solution properties of micelle networks formed by nonionic moieties covalently bound to a polyelectrolyte: salt effects on rheological behavior—Langmuir, 2000, Vol. 16, No. 12, 5324-5332";

"Stimuli responsive amphiphilic copolymers of sodium 2-(acrylamido)-2-methylpropanesulfonate and associative macromonomers—Polym. Preprint, Div. Polym. Chem. 1999, 40(2), 220-221".

The ethylenically unsaturated hydrophobic monomers of these particular copolymers are preferably chosen from the acrylates or acrylamides of formula (I) below:

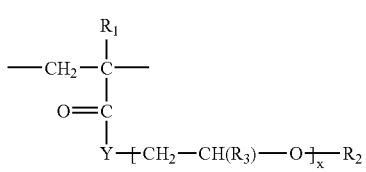

(I)

in which $R_1$ and $R_3$, which may be identical or different, denote a hydrogen atom or a linear or branched $C_1$-$C_6$ alkyl radical (preferably methyl); Y denotes O or NH; $R_2$ denotes a hydrophobic hydrocarbon-based radical containing at least from 6 to 50 carbon atoms, more preferably from 6 to 22 carbon atoms, even more preferably from 6 to 18 carbon atoms and more particularly from 12 to 18 carbon atoms; x denotes a number of moles of alkylene oxide and ranges from 0 to 100.

The radical $R_2$ is preferably chosen from linear $C_6$-$C_{18}$ alkyl radicals (for example n-hexyl, n-octyl, n-decyl, n-hexadecyl and n-dodecyl) and branched or cyclic $C_6$-$C_{18}$ alkyl radicals (for example cyclododecane ($C_{12}$) or adamantane ($C_{10}$)); $C_6$-$C_{18}$ alkylperfluoro radicals (for example the group of formula —$(CH_2)_2$—$(CF_2)_9$—$CF_3$); the cholesteryl radical ($C_{27}$) or a cholesterol ester residue, for instance the cholesteryl oxyhexanoate group; aromatic polycyclic groups, for instance naphthalene or pyrene. Among these radicals, the ones that are more particularly preferred are linear alkyl radicals and more particularly the n-dodecyl radical.

According to one particularly preferred form of the invention, the monomer of formula (I) comprises at least one alkylene oxide unit ($x \geq 1$) and preferably a polyoxyalkylenated chain. The polyoxyalkylenated chain preferably consists of ethylene oxide units and/or of propylene oxide units and even more particularly consists of ethylene oxide units. The number of oxyalkylene units generally ranges from 3 to 100, more preferably from 3 to 50 and even more preferably from 7 to 25.

Among these polymers, mention may be made of:

crosslinked or noncrosslinked, neutralized or nornmeutralized copolymers comprising from 15% to 60% by weight of AMPS units and from 40% to 85% by weight of ($C_8$-$C_{16}$)alkyl(meth)acrylamide units or of ($C_8$-$C_{16}$)alkyl (meth)acrylate units relative to the polymer, such as those described in patent application EP-A-750 899;

terpolymers comprising from 10 mol % to 90 mol % of acrylamide units, from 0.1 mol % to 10 mol % of AMPS units and from 5 mol % to 80 mol % of n-($C_6$-$C_{18}$) alkylacrylamide units, such as those described in patent U.S. Pat. No. 5,089,578.

Mention may also be made of copolymers of totally neutralized AMPS and of dodecyl methacrylate, and also crosslinked and noncrosslinked copolymers of AMPS and of n-dodecylmethacrylamide, such as those described in the Morishima articles mentioned above.

Mention will be made more particularly of the copolymers consisting of 2-acrylamido-2-methylpropanesulfonic acid (AMPS) units of formula (II) below:

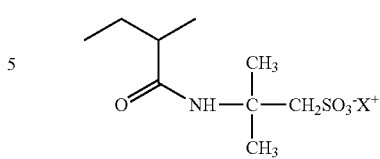

(II)

in which $X^+$ is a proton, an alkali metal cation, an alkaline-earth metal cation or the ammonium ion, and of units of formula (III) below:

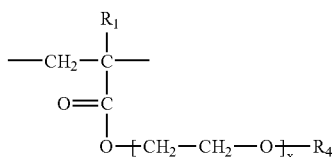

(III)

in which x denotes an integer ranging from 3 to 100, preferably from 5 to 80 and more preferably from 7 to 25; $R_1$ has the same meaning as that given above in formula (I) and $R_4$ denotes a linear or branched $C_6$-$C_{22}$ and more preferably $C_{10}$-$C_{22}$ alkyl.

The polymers that are particularly preferred are those for which x=25, $R_1$ denotes methyl and $R_4$ represents n-dodecyl; they are described in the Morishima articles mentioned above.

The polymers for which $X^+$ denotes sodium or ammonium are more particularly preferred.

The preferred amphiphilic polymers in accordance with the invention may be obtained according to the standard free-radical polymerization processes in the presence of one or more initiators such as, for example, azobisisobutyronitrile (AIBN), azobisdimethylvaleronitrile, ABAH (2,2-azobis[2-amidinopropane] hydrochloride), organic peroxides such as dilauryl peroxide, benzoyl peroxide, tert-butyl hydroperoxide, etc., mineral peroxide compounds such as potassium persulfate or ammonium persulfate, or $H_2O_2$ optionally in the presence of reducing agents.

The amphiphilic polymers are obtained especially by free-radical polymerization in tert-butanol medium in which they precipitate.

Using precipitation polymerization in tert-butanol, it is possible to obtain a size distribution of the polymer particles that is particularly favorable for its uses.

The size distribution of the polymer particles may be determined, for example, by laser diffraction or image analysis.

An advantageous distribution for this type of polymer, determined by image analysis, is as follows: 60.2% less than 423 microns, 52.0% less than 212 microns, 26.6% less than 106 microns, 2.6% less than 45 microns and 26.6% greater than 850 microns.

The reaction may be performed at a temperature of between 0 and 150° C., preferably between 10 and 100° C., either at atmospheric pressure or under reduced pressure. It may also be performed under inert atmosphere, and preferably under nitrogen.

According to this process 2-acrylamido-2-methylpropanesulfonic acid (AMPS) or a sodium or ammonium salt thereof was especially polymerized with a (meth)acrylic acid ester and a $C_{10}$-$C_{18}$ alcohol oxyethylenated with 8 mol of ethylene oxide (Genapol® C-080 from the company Hoechst/Clariant), a $C_{11}$ oxo alcohol oxyethylenated with 8 mol of ethylene oxide (Genapol® UD-080 from the company Hoechst/Clariant), a $C_{11}$ oxo alcohol oxyethylenated with 7 mol of ethylene oxide (Genapol® UD-070 from the company Hoechst/Clariant), a $C_{12}$-$C_{14}$ alcohol oxyethylenated with 7 mol of ethylene oxide (Genapol® LA-070 from the company Hoechst/Clariant), a $C_{12}$-$C_{14}$ alcohol oxyethylenated with 9 mol of ethylene oxide (Genapol® LA-090 from the company Hoechst/Clariant), a $C_{12}$-$C_{14}$ alcohol oxyethylenated with 11 mol of ethylene oxide (Genapol® LA-110 from the company Hoechst/Clariant), a $C_{16}$-$C_{18}$ alcohol oxyethylenated with 8 mol of ethylene oxide (Genapol® T-080 from the company Hoechst/Clariant), a $C_{16}$-$C_{18}$ alcohol oxyethylenated with 15 mol of ethylene oxide (Genapol® T-150 from the company Hoechst/Clariant), a $C_{16}$-$C_{18}$ alcohol oxyethylenated with 11 mol of ethylene oxide (Genapol® T-110 from the company Hoechst/Clariant), a $C_{16}$-$C_{18}$ alcohol oxyethylenated with 20 mol of ethylene oxide (Genapol® T-200 from the company Hoechst/Clariant), a $C_{16}$-$C_{18}$ alcohol oxyethylenated with 25 mol of ethylene oxide (Genapol® T-250 from the company Hoechst/Clariant), a $C_{18}$-$C_{22}$ alcohol oxyethylenated with 25 mol of ethylene oxide and/or a $C_{16}$-$C_{18}$ iso alcohol oxyethylenated with 25 mol of ethylene oxide.

The molar % concentration of the units of formula (II) and of the units of formula (III) in the polymers according to the invention will vary as a function of the desired cosmetic use and of the desired rheological properties of the formulation. It may range between 0.1 mol % and 99.9 mol %.

Preferably, for the most hydrophobic polymers, the molar proportion of units of formula (I) or (III) ranges from 50.1% to 99.9%, more particularly from 70% to 95% and even more particularly from 80% to 90%.

Preferably, for the sparingly hydrophobic polymers, the molar proportion of units of formula (I) or (III) ranges from 0.1% to 50%, more particularly from 5% to 25% and even more particularly from 10% to 20%.

The monomer distribution in the polymers of the invention may be, for example, alternating, block (including multiblock) or random.

According to the invention, it is preferable for the polymers to contain heat-sensitive pendant chains and for the aqueous solution thereof to have a viscosity that, beyond a certain threshold temperature, increases or remains virtually constant as the temperature increases.

Even more particularly, the preferred polymers are those whose aqueous solution has a viscosity that is low below a first threshold temperature and that, above this first threshold temperature, increases to a maximum as the temperature increases, and that, above a second threshold temperature, decreases again as the temperature increases. From this perspective, it is preferable for the viscosity of the polymer solutions below the first threshold temperature to be from 5% to 50%, in particular from 10% to 30% of the maximum viscosity at the second threshold temperature.

These polymers preferably lead in water to a phenomenon of demixing by heating, reflected by curves showing, as a function of the temperature and the concentration, a minimum known as the LCST (Lower Critical Solution Temperature).

The viscosities (measured at 25° C. using a Brookfield viscometer, needle No. 7) of the aqueous 1% solutions preferably range from 20 000 mPa·s to 100 000 mPa·s and more particularly from 60 000 mPa·s to 70 000 mPa·s.

The amphiphilic polymers in accordance with the invention are present in the compositions in concentrations ranging from 0.01% to 30% by weight of active material, more preferably from 0.1% to 10% of active material, even more preferably from 0.1% to 5% by weight of active material and even more particularly from 0.5% to 2% by weight.

Oxidation Dyes

The oxidation dyes that may be used according to the invention are chosen from oxidation bases and/or couplers.

Preferably, the compositions according to the invention contain at least one oxidation base.

The oxidation bases that may be used in the context of the present invention are chosen from those conventionally known in oxidation dyeing, and among which mention may be made in particular of the ortho- and para-phenylenediamines, double bases, ortho- and para-aminophenols and heterocyclic bases below, and also the addition salts thereof with an acid.

Mention may be made in particular of:

(I) the para-phenylenediamines of formula (I) below, and the addition salts thereof with an acid:

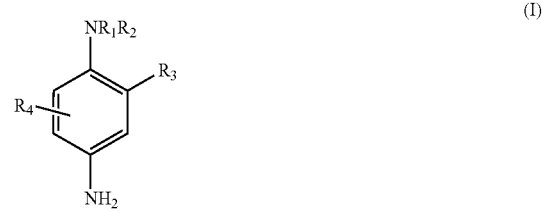

in which:

$R_1$ represents a hydrogen atom, a $C_1$-$C_4$ alkyl radical, a $C_1$-$C_4$ monohydroxyalkyl radical, a $C_2$-$C_4$ polyhydroxyalkyl radical, a ($C_1$-$C_4$)alkoxy($C_1$-$C_4$)alkyl radical or a $C_1$-$C_4$ alkyl radical substituted with a nitrogenous, phenyl or 4'-aminophenyl group;

$R_2$ represents a hydrogen atom, a $C_1$-$C_4$ alkyl radical, a $C_1$-$C_4$ monohydroxyalkyl radical, a $C_2$-$C_4$ polyhydroxyalkyl radical, a ($C_1$-$C_4$)alkoxy($C_1$-$C_4$)alkyl radical or a $C_1$-$C_4$ alkyl radical substituted with a nitrogenous group;

$R_1$ and $R_2$ may also form, with the nitrogen atom that bears them, a 5- or 6-membered nitrogenous heterocycle optionally substituted with one or more alkyl, hydroxyl or ureido groups;

$R_3$ represents a hydrogen atom, a halogen atom such as a chlorine atom, a $C_1$-$C_4$ alkyl radical, a sulfo radical, a carboxy radical, a $C_1$-$C_4$ monohydroxyalkyl radical, a $C_1$-$C_4$ hydroxyalkoxy radical, an acetylamino($C_1$-$C_4$) alkoxy radical, a mesylamino($C_1$-$C_4$)-alkoxy radical or a carbamoylamino($C_1$-$C_4$)alkoxy radical, $R_4$ represents a hydrogen or halogen atom or a $C_1$-$C_4$ alkyl radical.

Among the nitrogenous groups of formula (I) above, mention may be made in particular of amino, mono($C_1$-$C_4$)alkylamino, di($C_1$-$C_4$)alkylamino, tri($C_1$-$C_4$)alkylamino, monohydroxy($C_1$-$C_4$)alkylamino, imidazolinium and ammonium radicals.

Among the para-phenylenediamines of formula (I) above, mention may be made more particularly of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylene diamine, N-(β-methoxyethyl)-para-phenylenediamine and 2-methyl-1-N-β-hydroxyethyl-para-phenylenediamine, and the addition salts thereof with an acid.

Among the para-phenylenediamines of formula (I) above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and the addition salts thereof with an acid are most particularly preferred.

(II) According to the invention, the term double bases is understood to refer to compounds containing at least two aromatic nuclei bearing amino and/or hydroxyl groups.

Among the double bases which can be used as oxidation bases in the dye compositions in accordance with the invention, mention may be made in particular of the compounds corresponding to formula (II) below, and the addition salts thereof with an acid:

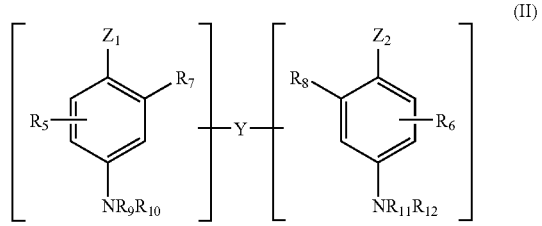

(II)

in which:

$Z_1$ and $Z_2$, which may be identical or different, represent a hydroxyl or —$NH_2$ radical which may be substituted with a $C_1$-$C_4$ alkyl radical or with a linker arm Y;

the linker arm Y represents a linear or branched alkylene chain containing from 1 to 14 carbon atoms, which may be interrupted by or terminated with one or more nitrogenous groups and/or one or more hetero atoms such as oxygen, sulfur or nitrogen atoms, and optionally substituted with one or more hydroxyl or $C_1$-$C_6$ alkoxy radicals;

$R_5$ and $R_6$ represent a hydrogen or halogen atom, a $C_1$-$C_4$ alkyl radical, a $C_1$-$C_4$ monohydroxyalkyl radical, a $C_2$-$C_4$ polyhydroxyalkyl radical, a $C_1$-$C_4$ aminoalkyl radical or a linker arm Y;

$R_7$, $R_8$, $R_9$, $R_{10}$, $R_{11}$, and $R_{12}$, which may be identical or different, represent a hydrogen atom, a linker arm Y or a $C_1$-$C_4$ alkyl radical;

it being understood that the compounds of formula (II) contain only one linker arm Y per molecule.

Among the nitrogenous groups of formula (II) above, mention may be made in particular of amino, mono($C_1$-$C_4$)alkylamino, di($C_1$-$C_4$)alkylamino, tri($C_1$-$C_4$)alkylamino, monohydroxy($C_1$-$C_4$)alkylamino, imidazolinium and ammonium radicals.

Among the double bases of formula (II) above, mention may be made more particularly of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-amino phenyl) tetramethylenediamine, N,N'-bis(β-hydroxyethyl)-N,N'-bis(4-aminophenyl) tetramethylenediamine, N,N'-bis(4-methylaminophenyl)tetramethylenediamine, N,N'-bis-(ethyl)-N,N'-bis(4'-amino-3'-methylphenyl)ethylenediamine and 1,8-bis(2,5-diamino phenoxy)-3,5-dioxaoctane, and the addition salts thereof with an acid.

Among these double bases of formula (II), N,N'-bis(β-hydroxyethyl)-N,N'-bis(4'-aminophenyl)-1,3-diaminopropanol and 1,8-bis(2,5-diaminophenoxy)-3,5-dioxaoctane, or one of the addition salts thereof with an acid, are particularly preferred.

(III) The para-aminophenols corresponding to formula (III) below, and the addition salts thereof with an acid:

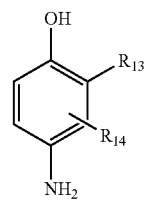

(III)

in which:

$R_{13}$ represents a hydrogen atom, a halogen atom, such as fluorine, or a $C_1$-$C_4$ alkyl, $C_1$-$C_4$ monohydroxyalkyl, ($C_1$-$C_4$)alkoxy($C_1$-$C_4$)alkyl, $C_1$-$C_4$ aminoalkyl or hydroxy($C_1$-$C_4$)-alkylamino($C_1$-$C_4$)alkyl radical, $R_{14}$ represents a hydrogen atom, a halogen atom, such as fluorine, or a $C_1$-$C_4$ alkyl, $C_1$-$C_4$ monohydroxyalkyl, $C_2$-$C_4$ polyhydroxyalkyl, $C_1$-$C_4$ aminoalkyl, $C_1$-$C_4$ cyanoalkyl or ($C_1$-$C_4$)alkoxy($C_1$-$C_4$)alkyl radical.

Among the para-aminophenols of formula (III) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxy methyl phenol, 4-amino-2-methoxymethylphenol, 4-amino-2-aminomethylphenol and 4-amino-2-(β-hydroxyethylaminomethyl)phenol, and the addition salts thereof with an acid.

(IV) The ortho-aminophenols that can be used as oxidation bases in the context of the present invention are chosen in particular from 2-aminophenol, 2-amino-1-hydroxy-5-methylbenzene, 2-amino-1-hydroxy-6-methylbenzene and 5-acetamido-2-aminophenol, and the addition salts thereof with an acid.

(V) Among the heterocyclic bases which can be used as oxidation bases in the dye compositions in accordance with the invention, mention may be made more particularly of pyridine derivatives, pyrimidine derivatives and pyrazole derivatives, and the addition salts thereof with an acid.

Among the pyridine derivatives, mention may be made more particularly of the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diamino pyridine, and the addition salts thereof with an acid.

Among the pyrimidine derivatives, mention may be made more particularly of the compounds described, for example, in German patent DE 2 359 399 or Japanese patents JP 88-169 571 and JP 91-10659 or patent application WO 96/15765, such as 2,4,5,6-tetraminopyrimidine, 4-hydroxy-2,5,6-triaminopyrimidine, 2-hydroxy-4,5,6-triamino pyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)amino]ethanol; 2-[(7-amino pyrazolo[1,5-a]pyrimidin-3-yl)(2-hydroxyethyl)amino]ethanol; 5,6-dimethylpyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine and 3-amino-5-methyl-7-imidazolyl propylaminopyrazolo[1,5-a]pyrimidine, and the addition salts thereof and the tautomeric forms thereof, when a tautomeric equilibrium exists, and the addition salts thereof with an acid.

Among the pyrazole derivatives, mention may be made more particularly of the compounds described in patents DE 3 843 892, DE 4 133 957 and patent applications WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-(β-hydroxyethyl)pyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

According to the present invention, the oxidation bases preferably represent from 0.0005% to 12% by weight approximately relative to the total weight of the composition and even more preferably from 0.005% to 8% by weight approximately relative to this weight.

The couplers which may be used in the dye composition according to the invention are those conventionally used in oxidation dye compositions, that is to say meta-aminophenols, meta-phenylenediamines, meta-diphenols, naphthols and heterocyclic couplers such as, for example, indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles and quinolines, and the addition salts thereof with an acid.

These couplers are chosen more particularly from 2,4-diamino-1-(β-hydroxyethyloxy)benzene, 2-methyl-5-aminophenol, 5-N-(β-hydroxyethyl)amino-2-methylphenol, 3-aminophenol, 2-methyl-3-amino-6-methylphenol, 3,5-diamino-2,6-dimethoxypyridine, 6-hydroxybenzomorpholine, 1-β-hydroxyethylamino-3,4-methylene dioxybenzene, 1-methyl-2,6-bis(β-hydroxyethylamino)benzene, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 1,3-bis(2,4-diamino phenoxy)propane, sesamol, 1-amino-2-methoxy-4,5-methylenedioxybenzene, α-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethyl pyrazolo[1,5-b]-1,2,4-triazole, and the addition salts thereof with an acid.

When they are present, these couplers preferably represent from 0.0001% to 10% by weight approximately relative to the total weight of the composition, and even more preferably from 0.005% to 5% by weight approximately.

In general, the addition salts with an acid of the oxidation bases and couplers are chosen in particular from the hydrochlorides, hydrobromides, sulfates, tartrates, lactates and acetates.

In addition to the oxidation dyes defined above, the composition according to the invention may also contain direct dyes to enrich the shades with glints. In this case, these direct dyes may be chosen in particular from neutral, cationic or anionic nitro, azo or anthraquinone dyes, in a weight proportion from about 0.001% to 20% and preferably from 0.01% to 10% relative to the total weight of the composition.

The dye composition and/or the oxidizing composition may also more particularly comprise at least one amphoteric or cationic polymer.

Cationic Polymers

For the purposes of the present invention, the expression "cationic polymer" denotes any polymer containing cationic groups and/or groups which may be ionized into cationic groups.

The cationic polymers which may be used in accordance with the present invention may be chosen from any of those already known per se as improving the cosmetic properties of the hair, namely, in particular, those described in patent application EP-A-337 354 and in French patents FR-2 270 846, 2 383 660, 2 598 611, 2 470 596 and 2 519 863.

The cationic polymers that are preferred are chosen from those containing units comprising primary, secondary, tertiary and/or quaternary amine groups, which may either form part of the main polymer chain or may be borne by a side substituent directly attached thereto.

The cationic polymers used generally have a number-average molecular mass of between 500 and $5\times10^6$ approximately and preferably between $10^3$ and $3\times10^6$ approximately.

Among the cationic polymers which may be mentioned more particularly are polymers of the polyamine, polyamino amide and polyquaternary ammonium type.

These are known products. They are described in particular in French patents 2 505 348 and 2 542 997. Among said polymers, mention may be made of:

(1) homopolymers or copolymers derived from acrylic or methacrylic esters or amides and comprising at least one of the units of formula (I), (II), (III) or (IV) below:

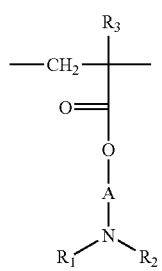

(I)

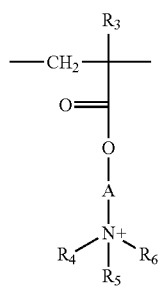

(II)

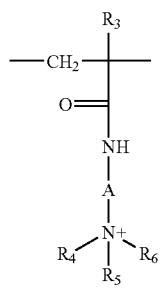

(III)

-continued

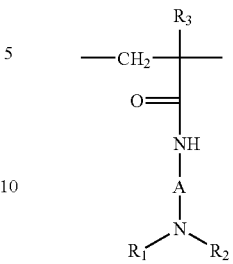

(IV)

in which:

R$_3$, which may be identical or different, denote a hydrogen atom or a CH$_3$ radical;

A, which may be identical or different, represent a linear or branched alkyl group of 1 to 6 carbon atoms, preferably 2 or 3 carbon atoms, or a hydroxyalkyl group of 1 to 4 carbon atoms;

R$_4$, R$_5$ and R$_6$, which may be identical or different, represent an alkyl group containing from 1 to 18 carbon atoms or a benzyl radical and preferably an alkyl group containing from 1 to 6 carbon atoms;

R$_1$ and R$_2$, which may be identical or different, represent hydrogen or an alkyl group containing from 1 to 6 carbon atoms, and preferably methyl or ethyl;

X denotes an anion derived from an inorganic or organic acid, such as a methosulfate anion or a halide such as chloride or bromide.

The polymers of family (1) can also contain one or more units derived from comonomers which may be chosen from the family of acrylamides, methacrylamides, diacetoneacrylamides, acrylamides and methacrylamides substituted on the nitrogen with lower (C$_1$-C$_4$) alkyls, acrylic or methacrylic acids or esters thereof, vinyllactams such as vinylpyrrolidone or vinylcaprolactam, and vinyl esters.

Thus, among these polymers of family (1), mention may be made of:

copolymers of acrylamide and of dimethylaminoethyl methacrylate quaternized with dimethyl sulfate or with a dimethyl halide, such as the product sold under the name Hercofloc by the company Hercules, the copolymers of acrylamide and of methacryloyloxyethyltrimethylammonium chloride described, for example, in patent application EP-A-080 976 and sold under the name Bina Quat P 100 by the company Ciba Geigy, the copolymer of acrylamide and of methacryloyloxyethyltrimethylammonium methosulfate sold under the name Reten by the company Hercules, quaternized or nonquaternized vinylpyrrolidone/dialkylaminoalkyl acrylate or methacrylate copolymers, such as the products sold under the name "Gafquat" by the company ISP, such as, for example, "Gafquat 734" or "Gafquat 755", or alternatively the products known as "Copolymer 845, 958 and 937". These polymers are described in detail in French patents 2 077 143 and 2 393 573, dimethylaminoethyl methacrylate/vinylcaprolactam/vinylpyrrolidone terpolymers, such as the product sold under the name Gaffix VC 713 by the company ISP, vinylpyrrolidone/methacrylamidopropyldimethylamine copolymers sold in particular under the name Styleze CC 10 by ISP, and quaternized vinylpyrrolidone/dimethylaminopropyl-methacrylamide copolymers such as the product sold under the name "Gafquat HS 100" by the company ISP.

(2) The cellulose ether derivatives containing quaternary ammonium groups, described in French patent 1 492 597, and in particular the polymers sold under the names "JR" (JR 400, JR 125 and JR 30M) or "LR" (LR 400, or LR 30M) by the company Union Carbide Corporation. These polymers are also defined in the CTFA dictionary as quaternary ammoniums of hydroxyethylcellulose that has reacted with an epoxide substituted with a trimethylammonium group.

(3) Cationic cellulose derivatives such as cellulose copolymers or cellulose derivatives grafted with a water-soluble monomer of quaternary ammonium, and described in particular in U.S. Pat. No. 4,131,576, such as hydroxyalkylcelluloses, for instance hydroxymethyl-, hydroxyethyl- or hydroxypropylcelluloses grafted, in particular, with a methacryloyloxyethyltrimethylammonium, methacrylamidopropyltrimethylammonium or dimethyldiallylammonium salt.

The commercial products corresponding to this definition are more particularly the products sold under the names "Celquat L 200" and "Celquat H 100" by the company National Starch.

(4) The cationic polysaccharides described more particularly in U.S. Pat. Nos. 3,589,578 and 4,031,307, such as guar gums containing cationic trialkylammonium groups. Guar gums modified with a salt (e.g. chloride) of 2,3-epoxypropyltrimethylammonium are used, for example.

Such products are sold in particular under the trade names Jaguar C13 S, Jaguar C 15, Jaguar C 17 or Jaguar C162 by the company Meyhall.

(5) Polymers consisting of piperazinyl units and of divalent alkylene or hydroxyalkylene radicals containing straight or branched chains, optionally interrupted by oxygen, sulfur or nitrogen atoms or by aromatic or heterocyclic rings, and also the oxidation and/or quaternization products of these polymers. Such polymers are described, in particular, in French patents 2 162 025 and 2 280 361.

(6) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2 252 840 and 2 368 508.

(7) The polyamino amide derivatives resulting from the condensation of polyalkylene polyamines with polycarboxylic acids followed by alkylation with difunctional agents. Mention may be made, for example, of adipic acid/dialkylaminohydroxyalkyldialkylene-triamine polymers in which the alkyl radical contains from 1 to 4 carbon atoms and preferably denotes methyl, ethyl or propyl. Such polymers are described in particular in French patent 1 583 363.

Among these derivatives, mention may be made more particularly of the adipic acid/dimethylaminohydroxypropyl/diethylenetriamine polymers sold under the name "Cartaretine F, F4 or F8" by the company Sandoz.

(8) The polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The molar ratio between the polyalkylene polyamine and the dicarboxylic acid is between 0.8:1 and 1.4:1; the polyamino amide resulting therefrom is reacted with epichlorohydrin in a molar ratio of epichlorohydrin relative to the secondary amine group of the polyamino amide of between 0.5:1 and 1.8:1. Such polymers are described in particular in U.S. Pat. Nos. 3,227,615 and 2,961,347.

Polymers of this type are sold in particular under the name "Hercosett 57" by the company Hercules Inc. or alternatively under the name "PD 170" or "Delsette 101" by the company Hercules in the case of the adipic acid/epoxypropyl/diethylenetriamine copolymer.

(9) Cyclopolymers of alkyldiallylamine or of dialkyldiallylammonium, such as the homopolymers or copolymers containing, as main constituent of the chain, units corresponding to formula (V) or (VI):

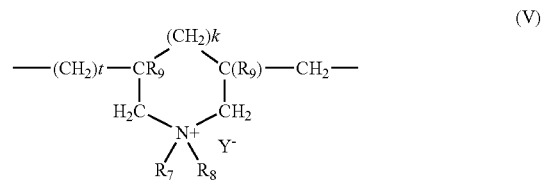

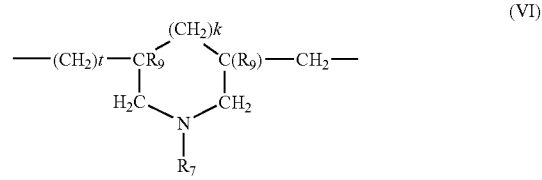

in which formulae k and t are equal to 0 or 1, the sum k+t being equal to 1; $R_9$ denotes a hydrogen atom or a methyl radical; $R_7$ and $R_8$, independently of each other, denote an alkyl group having from 1 to 8 carbon atoms, a hydroxyalkyl group in which the alkyl group preferably has 1 to 5 carbon atoms, a lower $C_1$-$C_4$ amidoalkyl group, or $R_7$ and $R_8$ can denote, together with the nitrogen atom to which they are attached, heterocyclic groups such as piperidyl or morpholinyl; $R_7$ and $R_8$, independently of each other, preferably denote an alkyl group having from 1 to 4 carbon atoms; $Y^-$ is an anion such as bromide, chloride, acetate, borate, citrate, tartrate, bisulfate, bisulfite, sulfate or phosphate. These polymers are described in particular in French patent 2 080 759 and in its Certificate of Addition 2 190 406.

Among the polymers defined above, mention may be made more particularly of the dimethyldiallylammonium chloride homopolymer sold under the name "Merquat 100" by the company Calgon (and its homologues of low weight-average molecular mass) and copolymers of diallyldimethylammonium chloride and of acrylamide, sold under the name "Merquat 550".

(10) The quaternary diammonium polymer containing repeating units corresponding to the formula:

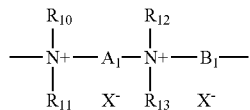 (VII)

in which formula (VII):

$R_{10}$, $R_{11}$, $R_{12}$ and $R_{13}$, which may be identical or different, represent aliphatic, alicyclic or arylaliphatic radicals containing from 1 to 20 carbon atoms or lower hydroxyalkylaliphatic radicals, or alternatively $R_{10}$, $R_{11}$, $R_{12}$ and $R_{13}$, together or separately, constitute, with the nitrogen atoms to which they are attached, heterocycles optionally containing a second hetero atom other than nitrogen, or alternatively $R_{10}$, $R_{11}$, $R_{12}$ and $R_{13}$ represent a linear or branched $C_1$-$C_6$ alkyl radical substituted with a nitrile, ester, acyl or amide group or a group —CO—O—$R_{14}$-D or —CO—NH—$R_{14}$-D where $R_{14}$ is an alkylene and D is a quaternary ammonium group;

$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from a mineral or organic acid;

$A_1$, $R_{10}$ and $R_{12}$ can form, with the two nitrogen atoms to which they are attached, a piperazine ring; in addition, if $A_1$ denotes a linear or branched, saturated or unsaturated alkylene or hydroxyalkylene radical, $B_1$ can also denote a group —$(CH_2)_n$—CO-D-OC—$(CH_2)_n$— in which D denotes:

a) a glycol residue of formula: —O-Z-O—, where Z denotes a linear or branched hydrocarbon-based radical or a group corresponding to one of the following formulae:

—$(CH_2$—$CH_2$—O$)_x$—$CH_2$—$CH_2$—

—$[CH_2$—$CH(CH_3)$—O$]_y$—$CH_2$—$CH(CH_3)$— where x and y denote an integer from 1 to 4, representing a defined and unique degree of polymerization or any number from 1 to 4 representing an average degree of polymerization;

b) a bis-secondary diamine residue such as a piperazine derivative;

c) a bis-primary diamine residue of formula: —NH—Y—NH—, where Y denotes a linear or branched hydrocarbon-based radical, or alternatively the divalent radical

—$CH_2$—$CH_2$—S—S—$CH_2$—$CH_2$—;

d) a ureylene group of formula: —NH—CO—NH—.

Preferably, $X^-$ is an anion such as chloride or bromide.

These polymers generally have a number-average molecular mass of between 1000 and 100 000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

It is more particularly possible to use polymers that consist of repeating units corresponding to formula (VIII) below:

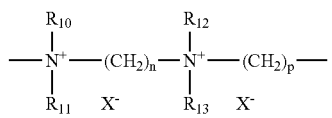 (VIII)

in which $R_{10}$, $R_{11}$, $R_{12}$ and $R_{13}$, which may be identical or different, denote an alkyl or hydroxyalkyl radical containing from 1 to 4 carbon atoms approximately, n and p are integers ranging from 2 to 20 approximately, and $X^-$ is an anion derived from a mineral or organic acid.

(11) Polyquaternary ammonium polymers consisting of repeating units of formula (IX):

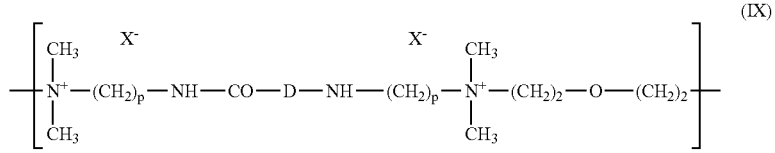 (IX)

in which p denotes an integer ranging from 1 to 6 approximately, D may be nothing or may represent a group —$(CH_2)_r$—CO— in which r denotes a number equal to 4 or to 7, $X^-$ is an anion.

Such polymers may be prepared according to the processes described in U.S. Pat. Nos. 4,157,388, 4,702,906 and 4,719,282. They are described in particular in patent application EP-A-122 324.

Among these products, mention may be made, for example, of "Mirapol A 15", "Mirapol AD1", "Mirapol AZ1" and "Mirapol 175" sold by the company Miranol.

(12) Quaternary polymers of vinylpyrrolidone and of vinylimidazole, such as, for example, the products sold under the names Luviquat FC 905, FC 550 and FC 370 by the company BASF.

(13) Polyamines such as Polyquart H sold by Henkel, which are given under the reference name "Polyethylene glycol (15) tallow polyamine" in the CTFA dictionary.

(14) Crosslinked methacryloyloxy($C_1$-$C_4$)alkyltri($C_1$-$C_4$) alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with an olefinically unsaturated compound, in particular methylenebisacrylamide. A crosslinked acrylamide/methacryloyl-oxyethyltrimethylammonium chloride copolymer (20/80 by weight) in the form of a dispersion containing 50% by weight of said copolymer in mineral oil can be used more particularly. This dispersion is sold under the name "Salcare® SC 92" by the company Allied Colloids. A crosslinked methacryloyloxyethyltrimethylammonium chloride homopolymer containing about 50% by weight of the homopolymer in mineral oil or in a liquid ester can also be used. These dispersions are sold under the names "Salcare® SC 95" and "Salcare® SC 96" by the company Allied Colloids.

Other cationic polymers which can be used in the context of the invention are polyalkyleneimines, in particular polyethyleneimines, polymers containing vinylpyridine or vinylpyridinium units, condensates of polyamines and of epichlorohydrin, quaternary polyureylenes and chitin derivatives.

Among all the cationic polymers which may be used in the context of the present invention, it is preferred to use the polymers of families (1), (9), (10), (11) and (14) and even more preferably the polymers consisting of repeating units of formulae (W) and (U) below:

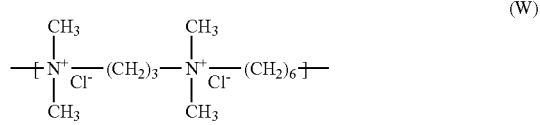

(W)

and in particular those whose weight-average molar mass, determined by gel permeation chromatography, is between 9500 and 9900;

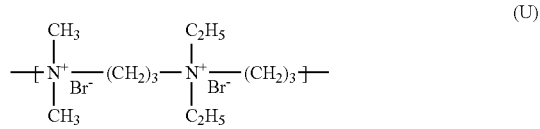

(U)

and in particular those whose weight-average molar mass, determined by gel permeation chromatography, is about 1200.

The concentration of cationic polymer in the composition according to the present invention may range from 0.01% to 10% by weight relative to the total weight of the composition, preferably from 0.05% to 5% and even more preferably from 0.1% to 3%.

Amphoteric Polymers

The amphoteric polymers which may be used in accordance with the present invention may be chosen from polymers comprising units K and M randomly distributed in the polymer chain, in which K denotes a unit derived from a monomer comprising at least one basic nitrogen atom and M denotes a unit derived from an acidic monomer comprising one or more carboxylic or sulfonic groups, or alternatively K and M may denote groups derived from zwitterionic carboxybetaine or sulfobetaine monomers;

K and M may also denote a cationic polymer chain comprising primary, secondary, tertiary or quaternary amine groups, in which at least one of the amine groups bears a carboxylic or sulfonic group linked via a hydrocarbon-based radical, or alternatively K and M form part of a chain of a polymer containing an α,β-dicarboxylic ethylene unit in which one of the carboxylic groups has been made to react with a polyamine comprising one or more primary or secondary amine groups.

The amphoteric polymers corresponding to the above definition that are more particularly preferred are chosen from the following polymers:

(1) polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylate and acrylate, dialkylaminoalkylmethacrylamide and -acrylamide. Such compounds are described in U.S. Pat. No. 3,836,537.

Mention may also be made of the sodium acrylate/acrylamidopropyl trimethylammonium chloride copolymer sold under the name Polyquart KE 3033 by the company Henkel.

The vinyl compound may also be a dialkyldiallylammonium salt such as dimethyldiallylammonium chloride. The copolymers of acrylic acid and of the latter monomer are sold under the names Merquat 280, Merquat 295 and Merquat Plus 3330 by the company Calgon.

(2) polymers containing units derived from:
a) at least one monomer chosen from acrylamides and methacrylamides substituted on the nitrogen with an alkyl radical,
b) at least one acidic comonomer containing one or more reactive carboxylic groups, and
c) at least one basic comonomer such as esters containing primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides which are more particularly preferred according to the invention are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid and fumaric acid and alkyl monoesters, having 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer such as the products sold under the name Amphomer or Lovocryl 47 by the company National Starch are particularly used.

(3) crosslinked and alkylated polyamino amides partially or totally derived from polyamino amides of general formula:

(X)

in which $R_{19}$ represents a divalent radical derived from a saturated dicarboxylic acid, a mono- or dicarboxylic aliphatic acid containing an ethylenic double bond, an ester of a lower alkanol, having 1 to 6 carbon atoms, of these acids or a radical derived from the addition of any one of said acids to a bis(primary) or bis(secondary) amine, and Z denotes a bis(primary), mono- or bis(secondary) polyalkylene-polyamine radical and preferably represents:
a) in proportions of from 60 to 100 mol %, the radical

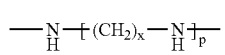
(XI)

where x=2 and p=2 or 3, or alternatively x=3 and p=2 this radical being derived from diethylenetriamine, from triethylenetetraamine or from dipropylenetriamine;
b) in proportions of from 0 to 40 mol %, the radical (XI) above in which x=2 and p=1 and which is derived from ethylenediamine, or the radical derived from piperazine:

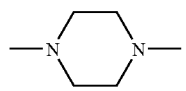

c) in proportions of from 0 to 20 mol %, the —NH—(CH$_2$)$_6$—NH— radical derived from hexamethylenediamine, these polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid and 2,4,4-trimethyladipic acid, terephthalic acid and acids containing an ethylenic double bond such as, for example, acrylic acid, methacrylic acid and itaconic acid.

The alkane sultones used in the alkylation are preferably propane sultone or butane sultone, and the salts of the alkylating agents are preferably the sodium or potassium salts.

(4) polymers containing zwitterionic units of formula:

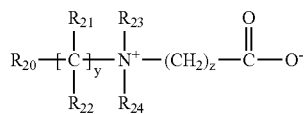
(XII)

in which R$_{20}$ denotes a polymerizable unsaturated group such as an acrylate, methacrylate, acrylamide or methacrylamide group, y and z represent an integer from 1 to 3, R$_{21}$, and R$_{22}$ represent a hydrogen atom, methyl, ethyl or propyl, R$_{23}$ and R$_{24}$ represent a hydrogen atom or an alkyl radical such that the sum of the carbon atoms in R$_{23}$ and R$_{24}$ does not exceed 10.

The polymers comprising such units can also contain units derived from nonzwitterionic monomers such as dimethyl or diethylaminoethyl acrylate or methacrylate or alkyl acrylates or methacrylates, acrylamides or methacrylamides or vinyl acetate.

By way of example, mention may be made of the copolymer of butyl methacrylate/dimethylcarboxymethylammonioethyl methacrylate such as the product sold under the name Diaformer Z301 by the company Sandoz.

(5) polymers derived from chitosan, described in particular in French patent No. 2 137 684 or U.S. Pat. No. 3,879,376, containing monomer units corresponding to formulae (XIII), (XIV) and (XV) below:

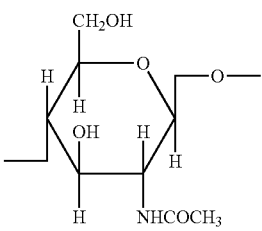
(XIII)

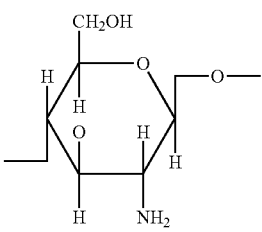
(XIV)

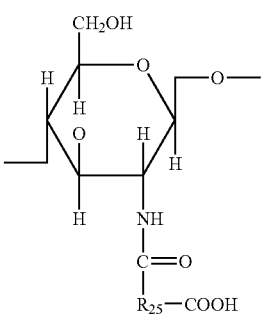
(XV)

the unit (XIII) being present in proportions of between 0 and 30%, the unit (XIV) in proportions of between 5% and 50% and the unit (XV) in proportions of between 30% and 90%, it being understood that, in this unit (XV), R$_{25}$ represents a radical of formula:

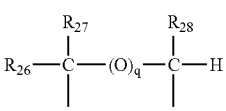

in which q denotes zero or 1;

if q=0, R$_{26}$, R$_{27}$ and R$_{28}$, which may be identical or different, each represent a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulfonic groups, an alkylthio residue in which the alkyl group bears an amino residue, at least one of the radicals R$_{26}$, R$_{27}$ and R$_{28}$ being, in this case, a hydrogen atom;

or, if q=1, R$_{26}$, R$_{27}$ and R$_{28}$ each represent a hydrogen atom, and also the salts formed by these compounds with bases or acids.

Polymers of this type that are more particularly preferred comprise from 0 to 20% by weight of units (XIII), from 40% to 50% by weight of units (XIV) and from 40% to 50% by weight of units (XV) in which $R_{25}$ denotes the radical —$CH_2$—$CH_2$—.

(6) polymers derived from the N-carboxyalkylation of chitosan, such as N-carboxymethylchitosan or N-carboxybutylchitosan sold under the name "Evalsan" by the company Jan Dekker.

(7) polymers corresponding to the general formula (XI) as described, for example, in French patent 1 400 366:

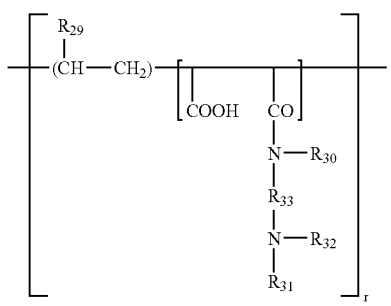

(XVI)

in which $R_{29}$ represents a hydrogen atom, a $CH_3O$, $CH_3CH_2O$ or phenyl radical, $R_{30}$ denotes hydrogen or a lower alkyl radical such as methyl or ethyl, $R_{31}$ denotes hydrogen or a lower alkyl radical such as methyl or ethyl, $R_{32}$ denotes a lower alkyl radical such as methyl or ethyl or a radical corresponding to the formula: —$R_{33}$—$N(R_{31})_2$, $R_{33}$ representing a —$CH_2$—$CH_2$—, —$CH_2$—$CH_2$—$CH_2$— or —$CH_2$—$CH(CH_3)$— group, $R_{31}$, having the meanings mentioned above, and also the higher homologues of these radicals and containing up to 6 carbon atoms, r is such that the molecular weight is between 500 and 6 000 000 and preferably between 1000 and 1 000 000.

(8) amphoteric polymers of the type -D-X-D-X- chosen from:

a) polymers obtained by the action of chloroacetic acid or sodium chloroacetate on compounds containing at least one unit of formula:

-D-X-D-X-D- (XVII)

where D denotes a radical

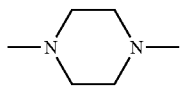

and X denotes the symbol E or E', E or E', which may be identical or different, denote a divalent radical which is an alkylene radical with a straight or branched chain containing up to 7 carbon atoms in the main chain, which is unsubstituted or substituted with hydroxyl groups and which can contain, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) polymers of formula:

-D-X-D-X- (XVIII)

where D denotes a radical

and X denotes the symbol E or E' and at least once E'; E having the meaning given above and E' being a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) ($C_1$-$C_5$)alkyl vinyl ether/maleic anhydride copolymers partially modified by semiamidation with an N,N-dialkylaminoalkylamine such as N,N-dimethylamino-propylamine or by semiesterification with an N,N-dialkanolamine. These copolymers can also contain other vinyl comonomers such as vinylcaprolactam.

The amphoteric polymers that are particularly preferred according to the invention are those of family (1).

According to the invention, the amphoteric polymer(s) may represent from 0.01% to 10% by weight, preferably from 0.05% to 5% by weight and even more preferably from 0.1% to 3% by weight relative to the total weight of the composition.

The compositions of the invention preferably comprise one or more surfactants.

The surfactants may be chosen, without discrimination, alone or as mixtures, from anionic, amphoteric, nonionic, zwitterionic and cationic surfactants.

The surfactants that are suitable for carrying out the present invention are especially the following:

(i) Anionic Surfactant(s):

By way of example of anionic surfactants which can be used, alone or as mixtures, in the context of the present invention, mention may be made in particular (nonlimiting list) of salts (in particular alkali metal salts, especially sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; ($C_6$-$C_{24}$) alkyl sulfosuccinates, ($C_6$-$C_{24}$)alkyl ether sulfosuccinates, ($C_6$-$C_{24}$)alkylamide sulfosuccinates; ($C_6$-$C_{24}$)alkyl sulfoacetates; ($C_6$-$C_{24}$)acyl sarcosinates; and ($C_6$-$C_{24}$)acyl glutamates. It is also possible to use ($C_6$-$C_{24}$)alkylpolyglycoside carboxylic esters such as alkylglucoside citrates, alkylpoly-glycoside tartrates and alkylpolyglycoside sulfosuccinates, alkylsulfosuccinamates; acyl isethionates and N-acyl taurates, the alkyl or acyl radical of all of these different compounds preferably containing from 12 to 20 carbon atoms and the aryl radical preferably denoting a phenyl or benzyl group. Among the anionic surfactants which can also be used, mention may also be made of fatty acid salts such as oleic, ricinoleic, palmitic and stearic acid salts, coconut oil acid or hydrogenated coconut oil acid; acyl lactylates in which the acyl radical contains 8 to 20 carbon atoms. It is also possible to use alkyl D-galactoside uronic acids and their salts, polyoxyalkylenated ($C_6$-$C_{24}$)alkyl ether carboxylic acids, polyoxyalkylenated ($C_6$-$C_{24}$)alkylaryl ether carboxylic acids, polyoxyalkylenated ($C_6$-$C_{24}$)alkylamido ether carboxylic acids and their salts, in particular those containing from 2 to 50 alkylene oxide groups, in particular ethylene oxide groups, and mixtures thereof.

(ii) Nonionic Surfactant(s):

The nonionic surfactants are, themselves also, compounds that are well known per se (see in particular in this respect "Handbook of Surfactants" by M. R. Porter, published by Blackie & Son (Glasgow and London), 1991, pp. 116-178) and their nature is not a critical factor in the context of the present invention. Thus, they can be chosen in particular from (nonlimiting list) polyethoxylated or polypropoxylated, alkylphenols, alpha-diols or alcohols, having a fatty chain containing, for example, 8 to 18 carbon atoms, it being possible for the number of ethylene oxide or propylene oxide groups to range in particular from 2 to 50. Mention may also be made of copolymers of ethylene oxide and of propylene oxide, condensates of ethylene oxide and of propylene oxide with fatty alcohols; polyethoxylated fatty amides preferably having from 2 to 30 mol of ethylene oxide, polyglycerolated fatty amides containing on average 1 to 5, and in particular 1.5 to 4, glycerol groups; polyethoxylated fatty amines preferably having 2 to 30 mol of ethylene oxide; oxyethylenated fatty acid esters of sorbitan having from 2 to 30 mol of ethylene oxide; fatty acid esters of sucrose, fatty acid esters of polyethylene glycol, alkylpolyglycosides, N-alkylglucamine derivatives, and amine oxides such as ($C_{10}$-$C_{14}$)alkylamine oxides or N-acylaminopropylmorpholine oxides. It will be noted that alkylpolyglycosides are nonionic surfactants that are particularly suitable within the context of the present invention.

(iii) Amphoteric or Zwitterionic Surfactant(s):

The amphoteric or zwitterionic surfactants, the nature of which is not a critical factor in the context of the present invention, can be, in particular (nonlimiting list), aliphatic secondary or tertiary amine derivatives in which the aliphatic radical is a linear or branched chain containing 8 to 18 carbon atoms and containing at least one water-solubilizing anionic group (for example carboxylate, sulfonate, sulfate, phosphate or phosphonate); mention may also be made of ($C_8$-$C_{20}$)alkylbetaines, sulfobetaines, ($C_8$-$C_{20}$)alkylamido($C_1$-$C_6$)alkylbetaines or ($C_8$-$C_{20}$)alkylamido($C_1$-$C_6$) alkylsulfobetaines.

Among the amine derivatives, mention may be made of the products sold under the name Miranol, as described in U.S. Pat. Nos. 2,528,378 and 2,781,354 and classified in the CTFA dictionary, 3rd edition, 1982, under the names Amphocarboxyglycinates and Amphocarboxypropionates, with the respective structures:

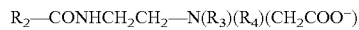

in which: $R_2$ denotes an alkyl radical of an acid $R_2$—COOH present in hydrolyzed coconut oil, a heptyl, nonyl or undecyl radical, $R_3$ denotes a beta-hydroxyethyl group and $R_4$ denotes a carboxymethyl group;

and 

in which:

B represents —$CH_2CH_2OX'$, C represents —$(CH_2)_z$—Y', with z=1 or 2,

X' denotes the —$CH_2CH_2$—COOH group or a hydrogen atom,

Y' denotes —COOH or the —$CH_2$—CHOH—$SO_3H$ radical, $R_2'$ denotes an alkyl radical of an acid $R_9$—COOH present in coconut oil or in hydrolyzed linseed oil, an alkyl radical, in particular a $C_7$, $C_9$, $C_{11}$ or $C_{13}$ alkyl radical, a $C_{17}$ alkyl radical and its iso form, or an unsaturated $C_{17}$ radical.

These compounds are classified in the CTFA dictionary, 5th edition, 1993, under the names Disodium Cocoamphodiacetate, Disodium Lauroamphodiacetate, Disodium Caprylamphodiacetate, Disodium Capryloamphodiacetate, Disodium Cocoampho-dipropionate, Disodium Lauroamphopropionate, Disodium Caprylamphodipropionate, Disodium Caprylamphodipropionate, Lauroamphodipropionic acid and Cocoampho-dipropionic acid.

By way of example, mention may be made of the cocoamphodiacetate sold under the trade name Miranol® C2M concentrate by the company Rhodia Chimie.

(iv) Cationic Surfactants:

Among the cationic surfactants, mention may be made in particular (nonlimiting list) of: salts of optionally polyoxyalkylenated primary, secondary or tertiary fatty amines; quaternary ammonium salts such as tetraalkylammonium, alkylamidoalkyltrialkyl-ammonium, trialkylbenzylammonium, trialkylhydroxyalkylammonium or alkylpyridinium chlorides or bromides; imidazoline derivatives; or amine oxides of cationic nature.

The amounts of surfactants present in the composition according to the invention can range from 0.01% to 40% and preferably from 0.1% to 30% relative to the total weight of the composition.

The medium for the composition that is suitable for dyeing is preferably an aqueous medium consisting of water and can advantageously contain cosmetically acceptable organic solvents including, more particularly, alcohols such as ethyl alcohol, isopropyl alcohol, benzyl alcohol and phenylethyl alcohol, or polyols or polyol ethers such as, for example, ethylene glycol monomethyl, monoethyl or monobutyl ether, propylene glycol or its ethers such as, for example, propylene glycol monomethyl ether, butylene glycol or dipropylene glycol, and also diethylene glycol alkyl ethers such as, for example, diethylene glycol monoethyl ether or monobutyl ether. The solvents may then be present in concentrations ranging from about 0.5% to about 20% and preferably between about 2% and 10% by weight relative to the total weight of the composition.

The dye composition according to the invention may also comprise an effective amount of other agents, known previously elsewhere in oxidation dyeing, such as various common adjuvants, for instance sequestering agents such as EDTA and etidronic acid, UV screening agents, waxes, volatile or nonvolatile, cyclic or linear or branched silicones, which are optionally organomodified (in particular with amine groups), preserving agents, ceramides, pseudoceramides, plant, mineral or synthetic oils, vitamins or provitamins, for instance panthenol, opacifiers, etc.

Said composition may also comprise reducing agents or antioxidants. These agents may be chosen in particular from sodium sulfite, thioglycolic acid, thiolactic acid, sodium bisulfite, dehydroascorbic acid, hydroquinone, 2-methylhydroquinone, tert-butylhydroquinone and homogentisic acid, and, in this case, they are generally present in amounts ranging from about 0.05% to 1.5% by weight relative to the total weight of the composition.

Needless to say, a person skilled in the art will take care to select the optional additional compound(s) mentioned above such that the advantageous properties intrinsically associated with the dye composition according to the invention are not, or are not substantially, adversely affected by the envisaged addition(s).

In the ready-to-use composition or in the oxidizing composition, the oxidizing agent is preferably chosen from [lacuna] urea peroxide, alkali metal bromates or ferricyanides, and persalts such as perborates and persulfates. It is particularly preferred to use hydrogen peroxide. This oxidizing agent advantageously consists of an aqueous hydrogen peroxide solution whose titer may range, more particularly, from about 1 to 40 volumes and even more preferably from about 5 to 40 volumes.

Oxidizing agents that may also be used are one or more redox enzymes such as laccases, peroxidases and 2-electron oxidoreductases (such as uricase), where appropriate in the presence of respective donor or cofactor thereof.

The pH of the ready-to-use composition applied to the keratin fibers [composition resulting from mixing together the dye composition and the oxidizing composition] is generally from 4 to 11. It is preferably between 6 and 10 and may be adjusted to the desired value using acidifying or basifying agents that are well known in the prior art in the dyeing of keratin fibers.

Among the basifying agents which may be mentioned, for example, are aqueous ammonia, alkali metal carbonates, alkanolamines such as monoethanolamine, diethanolamine and triethanolamine and derivatives thereof, oxyethylenated and/or oxypropylenated hydroxyalkylamines and ethylenediamines, sodium hydroxide, potassium hydroxide and the compounds of formula (XIX) below:

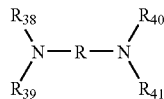

(XIX)

in which R is a propylene residue optionally substituted with a hydroxyl group or a $C_1$-$C_4$ alkyl radical; $R_{38}$, $R_{39}$, $R_{40}$ and $R_{41}$, which may be identical or different, represent a hydrogen atom, a $C_1$-$C_4$ alkyl radical or a $C_1$-$C_4$ hydroxyalkyl radical.

The acidifying agents are conventionally, for example, mineral or organic acids, for instance hydrochloric acid, orthophosphoric acid, carboxylic acids, for instance tartaric acid, citric acid or lactic acid, or sulfonic acids.

The dyeing process according to the invention preferably consists in applying the ready-to-use composition, prepared extemporaneously at the time of use from the dye composition and the oxidizing composition described above, to wet or dry keratin fibers, and leaving the composition to act for an action time preferably ranging from 1 to 60 minutes approximately and more preferably from 10 to 45 minutes approximately, rinsing the fibers and then optionally washing them with shampoo, and then rinsing them again and drying them.

One variant of this process consists in taking a composition comprising at least one oxidation dye that is free of amphiphilic polymer according to the invention, and another composition comprising at least one amphiphilic polymer, and mixing these two compositions with the oxidizing composition at the time of use, then applying the mixture obtained and leaving it to act as above.

According to said processes, each of these three compositions or the three compositions may also comprise at least one cationic or amphoteric polymer and at least one surfactant.

Concrete examples illustrating the invention are given below, without, however, being limiting in nature.

PREPARATION EXAMPLES

Preparation of Ethoxylated (Meth)Acrylic Esters:

These may especially be obtained by the action of glycidyl (meth)acrylate or (meth)acrylic acid or an alkyl (meth) acrylate or a (meth)acryloyl halide on an ethoxylated fatty alcohol. Nonlimiting examples that may be mentioned include the following preparations:

a) starting with glycidyl methacrylate and Genapol T-250;
b) starting with (meth)acrylic acid and Genapol UD-070;
c) starting with methyl (meth)acrylate and Genapol LA-090;
d) starting with (meth)acryloyl chloride and Genapol UD-070.

a) 500 g of Genapol T-250 and 75 g of glycidyl methacrylate are placed in a one-liter three-necked reactor equipped with a stirrer, a thermometer and a reflux condenser. The reaction mixture is heated at a temperature of 100° C. for 2 hours and the excess glycidyl methacrylate is removed by distillation under reduced pressure. The monomer obtained may be used for the polymerization without further purification.

b) 500 g of Genapol UD-070, 100 g of (meth)acrylic acid and p-toluenesulfonic acid as catalyst are placed in a one-liter three-necked reactor equipped with a stirrer, a thermometer and a reflux condenser. The reaction mixture is refluxed for 2 hours and the excess acid and the water formed during the reaction are separated out by distillation under reduced pressure. The monomer obtained may be used for the polymerization without further purification.

c) 500 g of Genapol LA-090, 100 g of methyl (meth) acrylate and 20 g of titanium tetraisopropoxide are placed in a one-liter three-necked reactor equipped with a stirrer, a thermometer and a reflux condenser. The reaction mixture is refluxed for 2 hours and, after separation by distilling off the alcohol formed, the remaining ester is distilled under reduced pressure. The monomer obtained may be used for the polymerization without further purification.

d) 500 g of Genapol UD-070, 110 g of (meth)acryloyl chloride and 50 g of sodium carbonate are placed in a one-liter three-necked reactor equipped with a stirrer, a thermometer and a reflux condenser. The reaction mixture is refluxed for 2 hours and the excess acid chloride is separated out by distillation under reduced pressure. The monomer obtained may be used for the polymerization without further purification.

Polymerization According to the Precipitation Method in Tert-butanol 500 ml of tert-butanol and the calculated amount of AMPS are placed in a 2-liter reactor equipped with a reflux condenser, a gas inlet, a thermometer and a stirrer. The mixture is neutralized by introducing $NH_3$, and the monomer prepared above is added to the reaction mixture. The reaction mixture is made inert by passing nitrogen or argon through, and, when the internal temperature has reached 60° C., the initiator (AIBN) is introduced to initiate the polymerization.

After a few minutes, the polymer thus prepared precipitates. The mixture is maintained at reflux for 2 hours, and the polymer is separated from the solvent by vacuum filtration and then dried under reduced pressure.

The following polymers were prepared in the manner described above:

(starting with the following reagents in amounts expressed in grams)

| | | | | |
|---|---|---|---|---|
| Genapol T-250 methacrylate | 10 | 20 | 30 | 97 |
| AMPS neutralized with $NH_3$ | 90 | 80 | 90 | 3 |
| Methylenebisacrylamide (crosslinking agent) | | | 1.5 | |
| Allyl methacrylate (crosslinking agent) | | 1.7 | | |
| TMPTA (crosslinking agent) | 1.8 | | | 1.8 |
| Azobisisobutyronitrile (initiator) | | | 1 | |
| Dilauryl peroxide (initiator) | 1 | 1 | | 1 |
| tert-Butanol | 300 | 300 | 300 | 300 |

EXAMPLES OF DYE COMPOSITIONS

The composition below was prepared:

(amounts expressed in grams)

| Oxidizing composition: | |
|---|---|
| Fatty alcohol | 2.3 |
| Oxyethylenated fatty alcohol | 0.6 |
| Fatty amide | 0.9 |
| Glycerol | 0.5 |
| Hydrogen peroxide | 7.5 |
| Fragrance | qs |
| Demineralized water | qs 100 |

| Dye composition: | |
|---|---|
| Acrylamido-2-methyl-2-propanesulfonic acid/n-dodecylacrylamide copolymer (3.5%/96.5%) 100% neutralized with sodium hydroxide | 1 |
| Isostearyl alcohol (Tego Alkanol 66 sold by the company Goldschmidt) | 12 |
| Benzyl alcohol | 4 |
| Polyethylene glycol containing 8 mol of ethylene oxide | 3 |
| Ethanol | 10 |
| para-Phenylenediamine | 0.54 |
| 2-Methyl-5-aminophenol | 0.615 |
| Sodium metabisulfite | 0.2 |
| Sequestering agent | qs |
| Aqueous ammonia containing 20% $NH_3$ | 10 |
| Demineralized water | qs 100 |

The dye composition was mixed, at the time of use, in a plastic bowl and for two minutes, with the oxidizing composition given above, in a proportion of one part of dye composition per one part of oxidizing composition.

The mixture obtained was applied to locks of natural hair containing 90% white hairs, and was left to act for 30 minutes.

The locks were then rinsed with water, washed with a standard shampoo, rinsed again with water and then dried.

The hair was dyed in a uniform purple shade.

Similar results were obtained by replacing the acrylamido-2-methyl-2-propanesulfonic acid/n-dodecylacrylamide copolymer neutralized with sodium hydroxide, of the above example, with a copolymer crosslinked with methylenebisacrylamide consisting of 75% by weight of AMPS units neutralized with $NH_3$ and 25% by weight of units of formula (III) in which $R_1$=H, $R_4$=$C_{16}$-$C_{18}$ and x=25.

Similar results were obtained by replacing the acrylamido-2-methyl-2-propanesulfonic acid/n-dodecylacrylamide copolymer neutralized with sodium hydroxide, of the above example, with a copolymer crosslinked with allyl methacrylate consisting of 90% by weight of AMPS units neutralized with $NH_3$ and 10% by weight of Genapol T-250 methacrylate units [units of formula (III) in which $R_1$=$CH_3$, $R_4$=$C_{16}$-$C_{18}$ and x=25], or with a copolymer crosslinked with allyl methacrylate consisting of 80% by weight of AMPS units neutralized with $NH_3$ and 20% by weight of Genapol T-250 methacrylate units [units of formula (III) in which $R_1$=$CH_3$, $R_4$=$C_{16}$-$C_{18}$ and x=25].

The invention claimed is:

1. An oxidation dye composition for keratin fibers, comprising:
   at least one oxidation dye in a medium that is suitable for dyeing and
   at least one amphiphilic copolymer comprising at least one ethylenically unsaturated monomer containing a sulfonic group, in free form or partially or totally neutralized form, and also at least one hydrophobic portion.

2. The composition as claimed in claim 1, wherein the hydrophobic portion of the amphiphilic copolymer comprises from 6 to 50 carbon atoms.

3. The composition as claimed in claim 2, wherein the hydrophobic portion of the amphiphilic copolymer comprises from 6 to 22 carbon atoms.

4. The composition as claimed in claim 3, wherein the hydrophobic portion of the amphiphilic copolymer comprises from 6 to 18 carbon atoms.

5. The composition as claimed in claim 4, wherein the hydrophobic portion of the amphiphilic copolymer comprises from 12 to 18 carbon atoms.

6. The composition as claimed in claim 1, wherein the amphiphilic copolymer is partially or totally neutralized with a mineral or organic base.

7. The composition as claimed in claim 1, wherein the amphiphilic copolymer has a number-average molecular weight ranging from 1,000 to 20,000,000 g/mol.

8. The composition as claimed in claim 7, wherein the number-average molecular weight ranges from 20,000 to 5,000,000 g/mol.

9. The composition as claimed in claim 8, wherein the number-average molecular weight ranges from 100,000 to 1,500,000 g/mol.

10. The composition as claimed in claim 1, wherein an aqueous solution at 1% by weight of said copolymer has, at a temperature of 25° C., a viscosity, measured using a Brookfield viscometer with a No. 7 needle, ranging from 20,000 mPa·s to 100,000 mPa·s.

11. The composition as claimed in claim 1, wherein the amphiphilic copolymer is prepared by free-radical precipitation polymerization in tert-butanol.

12. The composition as claimed in claim 1, wherein the amphiphilic copolymer is crosslinked or noncrosslinked.

13. The composition as claimed in claim 12, wherein the amphiphilic copolymer is crosslinked.

14. The composition as claimed in claim 13, wherein one or more crosslinking agents is a polyolefinically unsaturated compound.

15. The composition as claimed in claim 14, wherein one or more crosslinking agent is selected from the group consisting of methylenebisacrylamide, allyl methacrylate, and trimethylolpropane triacrylate (TMPTA).

16. The composition as claimed in claim 13, wherein the degree of crosslinking ranges from 0.01 mol % to 10 mol % relative to the polymer.

17. The composition as claimed in claim 1, wherein the ethylenically unsaturated monomer comprising a sulfonic group is selected from the group consisting of a vinylsulfonic acid, a styrenesulfonic acid, a (meth)acrylamido($C_1$-$C_{22}$)alkylsulfonic acid, and a N—($C_1$-$C_{22}$)alkyl(meth)acrylamido($C_1$-$C_{22}$)alkylsulfonic acid, and also partially or totally neutralized forms thereof.

18. The composition as claimed in claim 17, wherein the ethylenically unsaturated monomer comprising a sulfonic group is selected from the group consisting of acrylamidomethanesulfonic acid, acrylamidoethanesulfonic acid, acrylamidopropane sulfonic acid, 2-acrylamido-2-methylpropanesulfonic acid, methacrylamido-2-methylpropanesulfonic acid, 2-acrylamido-n-butanesulfonic acid, 2-acrylamido-2,4,4-trimethylpentanesulfonic acid, 2-methacrylamidododecylsulfonic acid, and 2-acrylamido-2,6-dimethyl-3-heptanesulfonic acid, and also partially or totally neutralized forms thereof.

19. The composition as claimed in claim 17, wherein the ethylenically unsaturated monomer comprising a sulfonic group is 2-acrylamido-2-methylpropanesulfonic acid (AMPS), and also partially or totally neutralized forms thereof.

20. The composition as claimed in claim 19, wherein the amphiphilic copolymer comprises random AMPS polymers modified by reaction with an n-mono($C_6$-$C_{22}$)alkylamine or a di-n-($C_6$-$C_{22}$)alkylamine.

21. The composition as claimed in claim 19, wherein the amphiphilic AMPS copolymer further comprises at least one ethylenically unsaturated monomer not comprising a fatty chain.

22. The composition as claimed in claim 20, wherein the ethylenically unsaturated monomer not comprising a fatty chain is or selected from the group consisting of a (meth)acrylic acid, a (meth)acrylamide, a vinylpyrrolidone, maleic anhydride, itaconic acid, maleic acid, and mixtures of these compounds; wherein said (meth)acrylic acid is an alkyl derivative thereof or an ester thereof as obtained with monoalcohols or mono-or polyalkylene glycols.

23. The composition as claimed in claim 1, wherein the ethylenically unsaturated hydrophobic monomer is an acrylate or an acrylamide of formula (I) below:

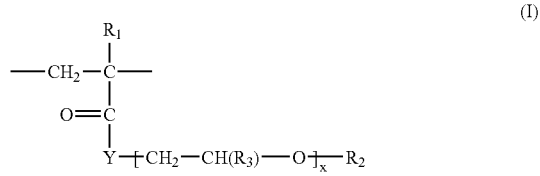

in which $R_1$ and $R_3$, which may be identical or different, denote a hydrogen atom or a linear or branched $C_1$-$C_6$ alkyl radical; Y denotes O or NH; $R_2$ denotes a hydrophobic hydrocarbon-based radical comprising at least from 6 to 50 carbon atoms; x denotes a number of moles of alkylene oxide and ranges from 0 to 100.

24. The composition as claimed in claim 23, wherein the hydrophobic radical $R_2$ is selected from the group consisting of a linear $C_6$-$C_{18}$ alkyl radical, a branched $C_6$-$C_{18}$ alkyl radical, a cyclic $C_6$-$C_{18}$ alkyl radical; a $C_6$-$C_{18}$ alkylperfluoro radical; a cholesteryl radical, an ester of a cholesterol radical; and an aromatic polycyclic group.

25. The composition as claimed in claim 23, wherein the monomer of formula (I) has a value of x that ranges from 1 to 100.

26. The composition as claimed in claim 23, wherein the monomer of formula (I) further comprises at least one polyoxyalkylenated chain.

27. The composition as claimed in claim 26, wherein the polyoxyalkylenated chain consists of ethylene oxide units and/or of propylene oxide units.

28. The composition as claimed in claim 27, wherein the polyoxyalkylenated chain consists of ethylene oxide units.

29. The composition as claimed in claim 23, wherein the number of oxyalkylene units ranges from 3 to 100.

30. The composition as claimed in claim 29, wherein the number of oxyalkylene units ranges from 3 to 50.

31. The composition as claimed in claim 30, wherein the number of oxyalkylene units ranges from 7 to 25.

32. The composition as claimed in claim 1, wherein the amphiphilic AMPS copolymer is selected from the group consisting of A and B;
 wherein A is defined by crosslinked or noncrosslinked, neutralized or nonneutralized copolymers comprising from 15% to 60% by weight of AMPS units and from 40% to 85% by weight of ($C_8$-$C_{16}$)alkyl(meth)acrylamide units or of ($C_8$-$C_{16}$)alkyl (meth)acrylate units relative to the polymer; and
 B is defined by terpolymers comprising from 10 mol % to 90 mol % of acrylamide units, from 0.1 mol % to 10 mol % of AMPS units and from 5 mol % to 80 mol % of n-($C_6$-$C_{18}$)alkylacrylamide units relative to the polymer.

33. The composition as claimed in claim 1, wherein the amphiphilic AMPS copolymer is selected from the group consisting of A and B; wherein
 A is defined by noncrosslinked copolymers of partially or totally neutralized AMPS and of n-dodecyl methacrylate; and
 B is defined by crosslinked or noncrosslinked copolymers of partially or totally neutralized AMPS and of n-dodecylmethacrylamide.

34. The composition as claimed in claim 1, wherein the amphiphilic AMPS copolymer is a copolymer consisting of 2-acrylamido-2-methylpropanesulfonic acid (AMPS) units of formula (II) below:

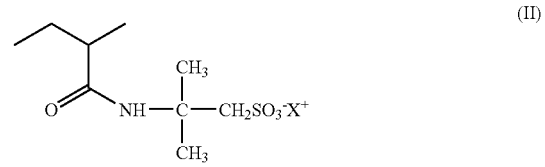

in which $X^+$ is a proton, an alkali metal cation, an alkaline-earth metal cation or an ammonium ion, and of units of formula (III) below:

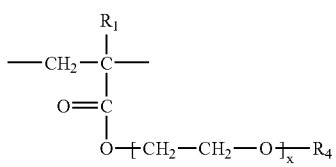

(III)

in which x denotes an integer ranging from 3 to 100; $R_1$ denotes a hydrogen atom or a linear or branched $C_1$-$C_6$ alkyl radical and $R_4$ denotes a linear or branched $C_6$-$C_{22}$.

35. The composition as claimed in claim 34, wherein x=25, $R_1$ is methyl and $R_4$ is n-dodecyl.

36. The composition as claimed in claim 23 wherein the molar percentage proportion of units of formula (I) in the polymers ranges from 50.1% to 99.9%.

37. The composition as claimed in claim 23 wherein the molar percentage proportion of units of formula (I) in the polymers ranges from 0.1% to 50%.

38. The composition as claimed in claim 1, wherein the amphiphilic copolymer is present in concentrations ranging from 0.01% to 30% by weight relative to the total weight of the composition.

39. The composition as claimed in claim 1, wherein the oxidation dye is an oxidation base and/or a coupler.

40. The composition as claimed in claim 39, wherein the composition comprises at least one oxidation base.

41. The composition as claimed in claim 39 wherein the oxidation base is selected from the group consisting of an ortho-phenylenediamine, a para-phenylenediamine, a double base, an ortho-aminophenol, a para-aminophenol, and a heterocyclic base, and also addition salts of these compounds with an acid.

42. The composition as claimed in claim 41, wherein the para-phenylenediamine is defined by structure (I) below:

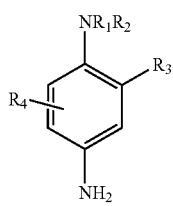

(I)

in which:

$R_1$ represents a hydrogen atom, a $C_1$-$C_4$ alkyl radical, a $C_1$-$C_4$ monohydroxyalkyl radical, a $C_2$-$C_4$ polyhydroxyalkyl radical, a $(C_1$-$C_4)$alkoxy$(C_1$-$C_4)$alkyl radical or a $C_1$-$C_4$ alkyl radical substituted with a nitrogenous, phenyl or 4'-aminophenyl group;

$R_2$ represents a hydrogen atom, a $C_1$-$C_4$ alkyl radical, a $C_1$-$C_4$ monohydroxyalkyl radical, a $C_2$-$C_4$ polyhydroxyalkyl radical, a $(C_1$-$C_4)$alkoxy$(C_1$-$C_4)$alkyl radical or a $C_1$-$C_4$ alkyl radical substituted with a nitrogenous group;

$R_1$ and $R_2$ may also form, with the nitrogen atom that bears them, a 5- or 6-membered nitrogenous heterocycle optionally substituted with one or more alkyl, hydroxyl or ureido groups;

$R_3$ represents a hydrogen atom, a halogen atom such as a chlorine atom, a $C_1$-$C_4$ alkyl radical, a sulfo radical, a carboxy radical, a $C_1$-$C_4$ monohydroxyalkyl radical, a $C_1$-$C_4$ hydroxyalkoxy radical, an acetylamino($C_1$-$C_4$) alkoxy radical, a mesylamino($C_1$-$C_4$)-alkoxy radical or a carbamoylamino($C_1$-$C_4$)alkoxy radical, $R_4$ represents a hydrogen or halogen atom or a $C_1$-$C_4$ alkyl radical.

43. The composition as claimed in claim 41, wherein the double base is defined by structure (II) below:

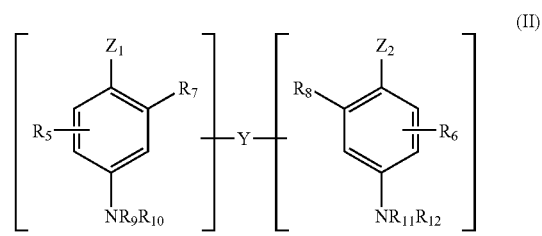

(II)

in which:

$Z_1$ and $Z_2$, which may be identical or different, represent a hydroxyl or —$NH_2$ radical which may be substituted with a $C_1$-$C_4$ alkyl radical or with a linker arm Y;

the linker arm Y represents a linear or branched alkylene chain containing from 1 to 14 carbon atoms, which may be interrupted by or terminated with one or more nitrogenous groups and/or one or more hetero atoms such as oxygen, sulfur or nitrogen atoms, and optionally substituted with one or more hydroxyl or $C_1$-$C_6$ alkoxy radicals;

$R_5$ and $R_6$ represent a hydrogen or halogen atom, a $C_1$-$C_4$ alkyl radical, a $C_1$-$C_4$ monohydroxyalkyl radical, a $C_2$-$C_4$ polyhydroxyalkyl radical, a $C_1$-$C_4$ aminoalkyl radical or a linker arm Y;

$R_7$, $R_8$, $R_9$, $R_{10}$, $R_{11}$ and $R_{12}$, which may be identical or different, represent a hydrogen atom, a linker arm Y or a $C_1$-$C_4$ alkyl radical;

it being understood that the compounds of formula (II) contain only one linker arm Y per molecule.

44. The composition as claimed in claim 41, wherein the para-aminophenol is defined by structure (III) below:

(III)

in which:

$R_{13}$ represents a hydrogen atom, a halogen atom, such as fluorine, or a $C_1$-$C_4$ alkyl, $C_1$-$C_4$ monohydroxyalkyl, $(C_1$-$C_4)$alkoxy$(C_1$-$C_4)$alkyl, $C_1$-$C_4$ aminoalkyl or hydroxy$(C_1$-$C_4)$-alkylamino$(C_1$-$C_4)$alkyl radical, $R_{14}$ represents a hydrogen atom, a halogen atom, such as fluorine, or a $C_1$-$C_4$ alkyl, $C_1$-$C_4$ monohydroxyalkyl, $C_2$-$C_4$ polyhydroxyalkyl, $C_1$-$C_4$ aminoalkyl, $C_1$-$C_4$ cyanoalkyl or $C_1$-$C_4$)alkoxy$(C_1$-$C_4$)alkyl radical.

45. The composition as claimed in claim 41, wherein heterocyclic base is selected from the group consisting of a pyridine derivative, a pyrimidine derivative a pyrazolopyrimidine, and a pyrazole derivative.

46. The composition as claimed in claim 41, wherein the oxidation base is present in concentrations ranging from 0.0005% to 12% by weight relative to the total weight of the composition.

47. The composition as claimed in claim 39, wherein the coupler is selected from the group consisting of a meta-phenyldiamine, a meta-aminophenol, a meta-diphenol, and a heterocyclic coupler, and the addition salts of these compounds with an acid.

48. The composition as claimed in claim 39, wherein the coupler is present in concentrations ranging from 0.0001% to 10% by weight relative to the total weight of the composition.

49. The composition as claimed in claim 39, wherein an acid addition salt of the oxidation dye comprises an anion which is selected from the group consisting of a chloride, a bromide, a sulfate, a hydrogensulfate, a tartrate, a lactate, and an acetate.

50. The composition as claimed in claim 1, wherein the composition further comprises direct dyes.

51. The composition as claimed in claim 1, wherein the composition further comprises at least one amphoteric polymer or one cationic polymer.

52. The composition as claimed in claim 51, wherein the cationic polymer is a polyquaternary ammonium consisting of repeating units corresponding to formula (W) below:

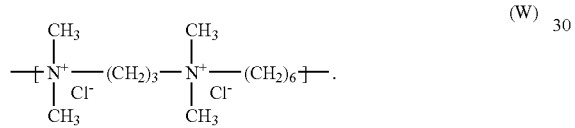

53. The composition as claimed in claim 51, wherein the cationic polymer is a polyquaternary ammonium consisting of repeating units corresponding to formula (U) below:

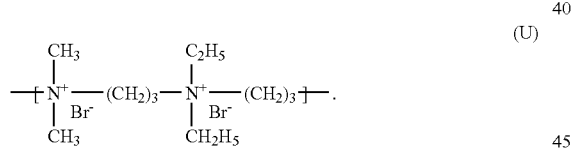

54. The composition as claimed in claim 51, wherein the amphoteric polymer is a copolymer comprising at least acrylic acid and a dimethyldiallylammonium salt as monomers.

55. The composition as claimed in claim 51, wherein the cationic or amphoteric polymer is present from 0.01% to 10% by weight relative to the total weight of the composition.

56. The composition as claimed in claim 1, wherein it comprises at least one surfactant chosen from anionic, cationic, nonionic and amphoteric surfactants.

57. The composition as claimed in claim 56, wherein the surfactants represent 0.01% to 40% by weight relative to the total weight of the composition.

58. The composition as claimed in claim 1, wherein the composition further comprises at least one reducing agent in amounts ranging from 0.05% to 3% by weight relative to the total weight of the composition.

59. The composition as claimed in claim 1, wherein the composition further comprises an oxidizing agent.

60. The composition as claimed in claim 59, wherein the oxidizing agent is selected from the group consisting of hydrogen peroxide, urea peroxide, an alkali metal bromate, an alkali metal ferricyanide, a persalt, and a redox enzyme; wherein said redox enzyme optionally comprises a respective donor or cofactor thereof.

61. The composition as claimed in claim 60, wherein the oxidizing agent is hydrogen peroxide.

62. The composition as claimed in claim 61, wherein the oxidizing agent is an aqueous hydrogen peroxide solution with a titer ranging from 1 to 40 volumes.

63. The composition as claimed in claim 59, wherein the composition has a pH ranging from 4 to 11.

64. A process for dyeing keratin fibers, which comprises:
applying to the keratin fibers at least one dye composition comprising at least one oxidation dye in a medium that is suitable for dyeing, the color being developed at alkaline, neutral or acidic pH using an oxidizing composition comprising at least one oxidizing agent, which is mixed with the dye composition just at the time of use or which is applied sequentially without intermediate rinsing, at least one amphiphilic copolymer as defined in claim 1 being present in the dye composition or in the oxidizing composition or in each of the two compositions.

65. The process as claimed in claim 64, which comprises applying to the wet or dry keratin fibers the composition prepared extemporaneously at the time of use from the dye composition and oxidizing composition, leaving the composition to act for an action time ranging from 1 to 60 minutes approximately;
rinsing the fibers and then optionally washing them with shampoo, and then rinsing them again and drying them.

66. A process for dyeing keratin fibers which comprises:
applying to the wet or dry keratin fibers a composition prepared extemporaneously at the time of use from a dye composition comprising at least one oxidation dye, another composition comprising at least one amphiphilic copolymer as defined according to claim 1, and an oxidizing composition,
leaving the composition to act for an action time ranging from 1 to 60 minutes approximately,
rinsing the fibers and then optionally
washing them with shampoo, and then rinsing them again and drying them.

67. The process as claimed in claim 66, wherein one or the other of said compositions also comprises at least one cationic or amphoteric polymer and at least one surfactant.

68. A two-compartment device or kit for dyeing keratin fibers, wherein one compartment comprises a dye composition comprising at least one oxidation dye in a medium that is suitable for dyeing, and another compartment comprises an oxidizing composition comprising an oxidizing agent in a medium that is suitable for dyeing, at least one amphiphilic copolymer as defined in claim 1 being present in the dye composition or in the oxidizing composition or in each of the two compositions.

69. A three-compartment device for dyeing keratin fibers, wherein a first compartment comprises a dye composition comprising at least one oxidation dye in a medium that is suitable for dyeing, a second compartment comprises an oxidizing composition comprising at least one oxidizing agent in a medium that is suitable for dyeing, and a third compartment comprises a composition comprising at least one amphiphilic copolymer as defined in claim 1, in a medium that is suitable for dyeing, the dye composition and/or the oxidizing composition also optionally comprises the amphiphilic polymer.

70. The composition as claimed in claim 13, wherein the degree of crosslinking ranges from 0.2 mol % to 2 mol % relative to the copolymer.

71. The composition as claimed in claim 1, wherein the ethylenically unsaturated hydrophobic monomer is an acrylate or an acrylamide of formula (I) below:

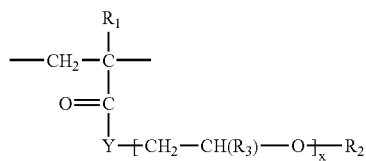

in which $R_1$ and $R_3$, which may be identical or different, denote a hydrogen atom or a methyl radical; Y denotes O or NH; $R_2$ denotes a hydrophobic hydrocarbon-based radical comprising at least from 6 to 50 carbon atoms; x denotes a number of moles of alkylene oxide and ranges from 0 to 100.

72. The composition as claimed in claim 1, wherein the ethylenically unsaturated hydrophobic monomer is an acrylate or an acrylamide of formula (I) below:

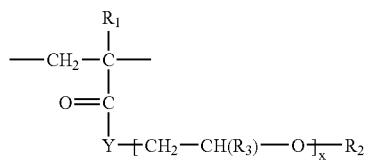

in which $R_1$ and $R_3$, which may be identical or different, denote a hydrogen atom or a linear or branched $C_1$-$C_6$ alkyl radical; Y denotes O or NH; $R_2$ denotes a hydrophobic hydrocarbon-based radical comprising at least from 6 to 22 carbon atoms; x denotes a number of moles of alkylene oxide and ranges from 0 to 100.

73. The composition as claimed in claim 1, wherein the ethylenically unsaturated hydrophobic monomer is an acrylate or an acrylamide of formula (I) below:

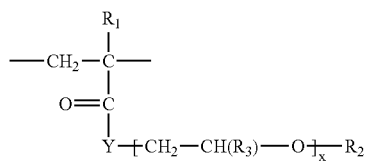

in which $R_1$ and $R_3$, which may be identical or different, denote a hydrogen atom or a linear or branched $C_1$-$C_6$ alkyl radical; Y denotes O or NH; $R_2$ denotes a hydrophobic hydrocarbon-based radical comprising at least from 6 to 18 carbon atoms; x denotes a number of moles of alkylene oxide and ranges from 0 to 100.

74. The composition as claimed in claim 1, wherein the ethylenically unsaturated hydrophobic monomer is an acrylate or an acrylamide of formula (I) below:

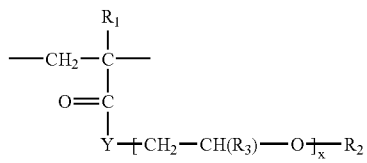

in which $R_1$ and $R_3$, which may be identical or different, denote a hydrogen atom or a linear or branched $C_1$-$C_6$ alkyl radical; Y denotes O or NH; $R_2$ denotes a hydrophobic hydrocarbon-based radical comprising at least from 12 to 18 carbon atoms; x denotes a number of moles of alkylene oxide and ranges from 0 to 100.

75. The composition as claimed in claim 1, wherein the amphiphilic AMPS copolymer is copolymer consisting of 2-acrylamido-2-methylpropanesulfonic acid (AMPS) units of formula (II) below:

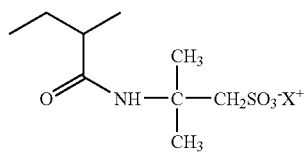

in which $X^+$ is a proton, an alkali metal cation, an alkaline-earth metal cation or an ammonium ion,
and of units of formula (III) below:

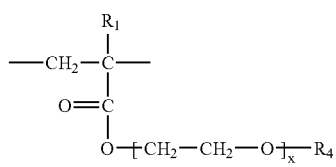

in which x denotes an integer ranging from 5 to 80; $R_1$ denotes a hydrogen atom or a linear or branched $C_1$-$C_6$ alkyl radical and $R_4$ denotes a linear or branched $C_6$-$C_{22}$.

76. The composition as claimed in claim 1, wherein the amphiphilic AMPS copolymer is a copolymer consisting of 2-acrylamido-2-methylpropanesulfonic acid (AMPS) units of formula (II) below:

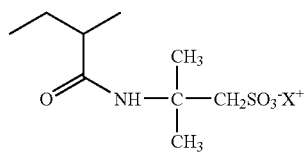

in which $X^+$ is a proton, an alkali metal cation, an alkaline-earth metal cation or an ammonium ion,
and of units of formula (III) below:

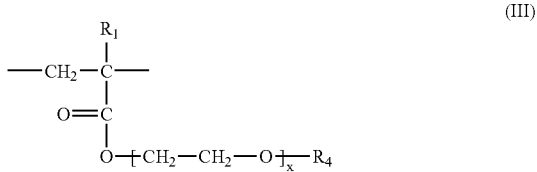

in which x denotes an integer ranging from 7 to 25; $R_1$ denotes a hydrogen atom or a linear or branched $C_1$-$C_6$ alkyl radical and $R_4$ denotes a linear or branched $C_6$-$C_{22}$.

77. The composition as claimed in claim 1, wherein the amphiphilic AMPS copolymer is a copolymer consisting of 2-acrylamido-2-methylpropanesulfonic acid (AMPS) units of formula (II) below:

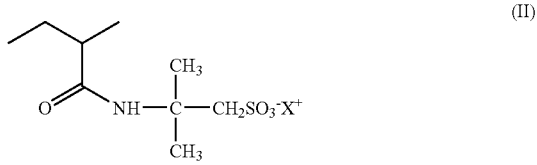

in which $X^+$ is a proton, an alkali metal cation, an alkaline-earth metal cation or an ammonium ion, and of units of formula (III) below:

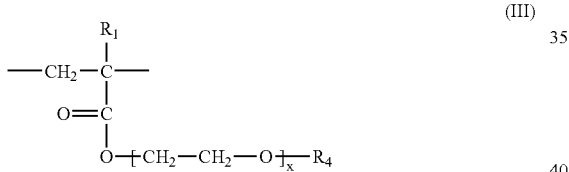

in which x denotes an integer ranging from 3 to 100; $R_1$ denotes a hydrogen atom or a linear or branched $C_1$-$C_6$ alkyl radical and $R_4$ denotes a linear or branched $C_{10}$-$C_{22}$.

78. The composition as claimed in claim 1, wherein the amphiphilic copolymer is present in concentrations ranging from 0.1% to 10% by weight relative to the total weight of the composition.

79. The composition as claimed in claim 1, wherein the amphiphilic copolymer is present in concentrations ranging from 0.1% to 5% by weight relative to the total weight of the composition.

80. The composition as claimed in claim 1, wherein the amphiphilic copolymer is present in concentrations ranging from 0.5% to 2% by weight relative to the total weight of the composition.

81. The composition as claimed in claim 51, wherein the cationic or amphoteric polymer is present from 0.05% to 5% by weight relative to the total weight of the composition.

82. The composition as claimed in claim 51, wherein the cationic or amphoteric polymer is present from 0.1% to 3% by weight relative to the total weight of the composition.

83. The composition as claimed in claim 56, wherein the surfactants represent 0.1% to 30% by weight relative to the total weight of the composition.

84. A process for dyeing keratin fibers, which comprises:
applying to the wet or dry keratin fibers a composition prepared extemporaneously at the time of use from a dye composition comprising at least one oxidation dye, another composition comprising at least one amphiphilic copolymer as defined according to claim 1, and an oxidizing composition,
leaving the composition to act for an action time ranging from 10 to 45 minutes approximately
rinsing the fibers and then optionally
washing them with shampoo, and then rinsing them again and drying them.

85. A process for dyeing human keratin fibers, which comprises:
applying to the wet or dry keratin fibers a composition prepared extemporaneously at the time of use from a dye composition comprising at least one oxidation dye, another composition comprising at least one amphiphilic copolymer as defined according to claim 1, and an oxidizing composition,
leaving the composition to act for an action time ranging from 1 to 60 minutes approximately
rinsing the fibers and then optionally
washing them with shampoo, and then rinsing them again and drying them.

86. A process for dyeing human keratin fibers, which comprises:
applying to the wet or dry keratin fibers a composition prepared extemporaneously at the time of use from a dye composition comprising at least one oxidation dye, another composition comprising at least one amphiphilic copolymer as defined according to claim 1, and an oxidizing composition,
leaving the composition to act for an action time ranging from 10 to 45 minutes approximately
rinsing the fibers and then optionally
washing them with shampoo, and then rinsing them again and drying them.

87. A two-compartment device or kit for dyeing human keratin fibers, wherein one compartment comprises a dye composition comprising at least one oxidation dye in a medium that is suitable for dyeing, and another compartment comprises an oxidizing composition comprising an oxidizing agent in a medium that is suitable for dyeing, at least one amphiphilic copolymer as defined in claim 1 being present in the dye composition or in the oxidizing composition or in each of the two compositions.

88. A three-compartment device for dyeing human keratin fibers, wherein a first compartment comprises a dye composition comprising at least one oxidation dye in a medium that is suitable for dyeing, a second compartment comprises an oxidizing composition comprising at least one oxidizing agent in a medium that is suitable for dyeing, and a third compartment comprises a composition comprising at least one amphiphilic copolymer as defined in claim 1, in a medium that is suitable for dyeing, the dye composition and/or the oxidizing composition also optionally comprises the amphilic polymer.

89. The oxidation dye composition according to claim 1, further comprising at least one UV screening agent.

* * * * *